US011318073B2

(12) United States Patent
Renock et al.

(10) Patent No.: US 11,318,073 B2
(45) Date of Patent: *May 3, 2022

(54) LOW SURFACTANT AEROSOL ANTIDANDRUFF COMPOSITION

(71) Applicant: The Procter & Gamble Company, Cincinnati, OH (US)

(72) Inventors: Sean Michael Renock, Loveland, OH (US); Eric Scott Johnson, Hamilton, OH (US); Debora W. Chang, Mason, OH (US); Sumanth Narahari Jamadagni, West Chester, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/170,498

(22) Filed: Oct. 25, 2018

(65) Prior Publication Data

US 2020/0000690 A1 Jan. 2, 2020

Related U.S. Application Data

(60) Provisional application No. 62/692,127, filed on Jun. 29, 2018.

(51) Int. Cl.
*A61K 8/04* (2006.01)
*A61K 8/31* (2006.01)
*A61K 8/37* (2006.01)
*A61K 8/46* (2006.01)
*A61K 8/49* (2006.01)
*A61K 8/891* (2006.01)
*A61Q 5/00* (2006.01)
*A61Q 5/02* (2006.01)

(52) U.S. Cl.
CPC ............... *A61K 8/046* (2013.01); *A61K 8/31* (2013.01); *A61K 8/315* (2013.01); *A61K 8/375* (2013.01); *A61K 8/463* (2013.01); *A61K 8/4926* (2013.01); *A61K 8/891* (2013.01); *A61Q 5/006* (2013.01); *A61Q 5/02* (2013.01)

(58) Field of Classification Search
CPC ...... A61K 8/046; A61K 8/315; A61K 8/4926; A61K 8/375; A61K 8/31; A61K 8/891; A61K 8/463; A61Q 5/006; A61Q 5/02
See application file for complete search history.

(56) References Cited

U.S. PATENT DOCUMENTS

| | | |
|---|---|---|
| 2,879,231 A | 3/1959 | Marshall |
| 3,709,437 A | 1/1973 | Wright |
| 3,950,532 A | 4/1976 | Bouillon et al. |
| 3,959,160 A | 5/1976 | Horsier et al. |
| 4,309,119 A | 1/1982 | Wittersheim |
| 4,329,334 A | 5/1982 | Su et al. |
| 4,686,254 A | 8/1987 | Lochhead et al. |
| 4,726,945 A | 2/1988 | Patel |
| 4,839,166 A | 6/1989 | Grollier et al. |
| 4,867,971 A | 9/1989 | Ryan et al. |
| 4,997,641 A | 3/1991 | Hartnett |
| 5,221,530 A | 6/1993 | Janchitraponvej et al. |
| 5,294,644 A | 3/1994 | Login et al. |
| 5,332,569 A | 7/1994 | Wood et al. |
| 5,364,031 A | 11/1994 | Taniguchi et al. |
| 5,374,421 A | 12/1994 | Tashiro |
| 5,409,695 A | 4/1995 | Abrutyn et al. |
| 5,415,810 A | 5/1995 | Lee et al. |
| 5,417,965 A | 5/1995 | Janchitraponvej et al. |
| 5,439,682 A | 8/1995 | Wivell |
| 5,441,659 A | 8/1995 | Minor |
| 5,500,217 A | 3/1996 | Austin et al. |
| 5,560,918 A | 10/1996 | Wivell |
| 5,578,298 A | 11/1996 | Berthiaume |
| 5,599,549 A | 2/1997 | Wivell |
| 5,624,666 A | 4/1997 | Coffindaffer et al. |
| 5,635,469 A | 6/1997 | Fowler et al. |
| 5,716,626 A | 2/1998 | Sakurai et al. |
| 5,747,436 A | 5/1998 | Patel et al. |
| 5,776,444 A | 7/1998 | Birtwistle et al. |
| 5,816,446 A | 10/1998 | Steindorf et al. |
| 5,830,440 A | 11/1998 | Sturla et al. |
| 5,853,618 A | 12/1998 | Barker |
| 5,902,225 A | 5/1999 | Monson |
| 5,925,603 A | 7/1999 | D'Angelo |
| 5,944,229 A | 8/1999 | Rokkjaer |
| 5,980,877 A | 11/1999 | Baravetto |
| 5,985,939 A | 11/1999 | Minor |
| 6,015,547 A | 1/2000 | Yam |
| 6,015,780 A | 1/2000 | Llosas Bigorra et al. |
| 6,020,303 A | 2/2000 | Cripe et al. |

(Continued)

FOREIGN PATENT DOCUMENTS

| | | |
|---|---|---|
| CA | 2078375 A1 | 3/1994 |
| CN | 1917853 A | 2/2007 |

(Continued)

OTHER PUBLICATIONS

"Natural Detangling Shampoo", Mintel Database, Sep. 13, 2017.
"Soda Shampoo", Mintel Database, Apr. 2015.
"Treatment Foam for Recurrent Scaling Conditions", Mintel Database, Aug. 2007.
All Final and Non-Final Office Actions for U.S. Appl. No. 16/156,045.
All Final and Non-Final Office Actions for U.S. Appl. No. 15/135,657.
All Final and Non-Final Office Actions for U.S. Appl. No. 15/135,663.
All Final and Non-Final Office Actions for U.S. Appl. No. 15/135,677.

(Continued)

*Primary Examiner* — Robert S Cabral
(74) *Attorney, Agent, or Firm* — Linda M. Sivik

(57) ABSTRACT

The present invention is directed to a foaming composition comprising from about 5% to about 13% total surfactant of one or more anionic surfactants; from 0.1% to about 2% of a surfactant soluble antidandruff active; from about 3% to about 15% of a blowing agent, wherein the foaming composition is at a pH of about 3.5 to 6.5.

29 Claims, 1 Drawing Sheet

(56) References Cited

U.S. PATENT DOCUMENTS

| | | |
|---|---|---|
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,153,569 A | 11/2000 | Halloran |
| 6,162,834 A | 12/2000 | Sebillotte-Arnaud et al. |
| 6,231,844 B1 | 5/2001 | Nambu |
| 6,268,431 B1 | 7/2001 | Snyder et al. |
| 6,284,225 B1 | 9/2001 | Bhatt |
| 6,329,331 B1 | 12/2001 | Aronson et al. |
| 6,335,312 B1 | 1/2002 | Coffindaffer et al. |
| 6,423,305 B1 | 7/2002 | Cauwet-Martin et al. |
| 6,451,300 B1 | 9/2002 | Dunlop et al. |
| 6,511,669 B1 | 1/2003 | Garnier et al. |
| 6,565,863 B1 | 5/2003 | Guillou et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop et al. |
| 6,716,455 B2 | 4/2004 | Birkel |
| 6,743,760 B1 | 6/2004 | Hardy et al. |
| 6,827,795 B1 | 12/2004 | Kasturi et al. |
| 6,897,253 B2 | 5/2005 | Schmucker-Castner |
| 6,930,078 B2 | 8/2005 | Wells |
| 6,992,054 B2 | 1/2006 | Lee et al. |
| 7,217,752 B2 | 5/2007 | Schmucker-Castner et al. |
| 7,220,408 B2 | 5/2007 | Decoster et al. |
| 7,223,385 B2 | 5/2007 | Gawtrey et al. |
| 7,485,289 B2 | 2/2009 | Gawtrey et al. |
| 7,504,094 B2 | 3/2009 | Decoster et al. |
| 7,531,497 B2 | 5/2009 | Midha et al. |
| 7,541,320 B2 | 6/2009 | Dabkowski et al. |
| 7,659,233 B2 | 2/2010 | Hurley et al. |
| 7,666,825 B2 | 2/2010 | Wagner et al. |
| 7,820,609 B2 | 10/2010 | Soffin et al. |
| 7,829,514 B2 | 11/2010 | Paul et al. |
| 7,928,053 B2 | 4/2011 | Hecht et al. |
| 7,977,288 B2 | 7/2011 | SenGupta |
| 8,084,407 B2 | 12/2011 | Soffin et al. |
| 8,088,721 B2 | 1/2012 | Soffin et al. |
| 8,119,168 B2 | 2/2012 | Johnson |
| 8,124,063 B2 | 2/2012 | Harichian et al. |
| 8,300,949 B2 | 10/2012 | Xu |
| 8,343,469 B2 | 1/2013 | Bierganns et al. |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,491,877 B2 | 7/2013 | Schwartz et al. |
| 8,580,725 B2 | 11/2013 | Kuhlman et al. |
| 8,609,600 B2 | 12/2013 | Warr et al. |
| 8,628,760 B2 | 1/2014 | Carter et al. |
| 8,629,095 B2 | 1/2014 | Deleersnyder |
| 8,653,014 B2 | 2/2014 | Hilvert |
| 8,675,919 B2 | 3/2014 | Maladen |
| 8,680,035 B2 | 3/2014 | Kuhlman et al. |
| 8,699,751 B2 | 4/2014 | Maladen |
| 8,709,385 B2 | 4/2014 | Tamarkin |
| 8,741,363 B2 | 6/2014 | Albrecht et al. |
| 8,771,765 B1 | 7/2014 | Fernandez |
| 8,795,635 B2 | 8/2014 | Tamarkin et al. |
| 8,883,698 B2 | 11/2014 | Scheibel et al. |
| 9,006,162 B1 | 4/2015 | Rizk |
| 9,186,642 B2 | 11/2015 | Dihora et al. |
| 9,265,727 B1 | 2/2016 | Lowenborg |
| 9,296,550 B2 | 3/2016 | Smith |
| 9,308,398 B2 | 4/2016 | Hutton et al. |
| 9,428,616 B2 | 8/2016 | Wagner |
| 9,512,275 B2 | 12/2016 | Wagner |
| 9,610,239 B2 | 4/2017 | Feng |
| 9,682,021 B2 | 6/2017 | Tamarkin et al. |
| 9,776,787 B2 | 10/2017 | Nakajima |
| 9,949,901 B2 | 4/2018 | Zhao et al. |
| 9,968,535 B2 | 5/2018 | Kitko |
| 9,968,537 B2 | 5/2018 | Sharma |
| 9,993,419 B2 | 6/2018 | Glenn, Jr. |
| 9,993,420 B2 | 6/2018 | Glenn, Jr. et al. |
| 10,311,575 B2 | 6/2019 | Stofel |
| 10,426,713 B2 | 10/2019 | Song |
| 10,441,519 B2 | 10/2019 | Zhao |
| 10,653,590 B2 | 5/2020 | Torres Rivera |
| 10,799,434 B2 | 10/2020 | Torres Rivera |
| 10,842,720 B2 | 11/2020 | Thompson |
| 10,881,597 B2 | 1/2021 | Lane et al. |
| 10,888,505 B2 | 1/2021 | Johnson |
| 10,912,732 B2 | 2/2021 | Gillis |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0083210 A1 | 5/2003 | Goldberg |
| 2003/0108501 A1 | 6/2003 | Hofrichter |
| 2003/0147842 A1 | 8/2003 | Restle et al. |
| 2003/0154561 A1 | 8/2003 | Patel |
| 2003/0161802 A1 | 8/2003 | Flammer |
| 2003/0180246 A1 | 9/2003 | Frantz et al. |
| 2003/0185867 A1 | 10/2003 | Kerschner et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0144863 A1 | 7/2004 | Kendrick |
| 2004/0229963 A1 | 11/2004 | Stephane |
| 2004/0234484 A1 | 11/2004 | Peffly |
| 2004/0235689 A1 | 11/2004 | Sakai et al. |
| 2005/0020468 A1 | 1/2005 | Frantz et al. |
| 2005/0136011 A1 | 6/2005 | Nekludoff |
| 2005/0152863 A1 | 7/2005 | Brautigam |
| 2005/0201967 A1 | 9/2005 | Albrecht et al. |
| 2005/0202984 A1 | 9/2005 | Schwartz et al. |
| 2005/0233929 A1 | 10/2005 | Queen |
| 2006/0002880 A1 | 1/2006 | Peffly |
| 2006/0030509 A1 | 2/2006 | Modi |
| 2006/0034778 A1 | 2/2006 | Kitano et al. |
| 2006/0057075 A1 | 3/2006 | Arkin et al. |
| 2006/0057097 A1 | 3/2006 | Derici |
| 2006/0079417 A1 | 4/2006 | Wagner |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0090777 A1 | 5/2006 | Hecht et al. |
| 2006/0110415 A1 | 5/2006 | Gupta |
| 2006/0120982 A1 | 6/2006 | Derici et al. |
| 2006/0120988 A1 | 6/2006 | Bailey et al. |
| 2006/0135397 A1 | 6/2006 | Bissey-beugras |
| 2006/0183662 A1 | 8/2006 | Crotty et al. |
| 2006/0210139 A1 | 9/2006 | Carroll |
| 2006/0229227 A1 | 10/2006 | Goldman |
| 2006/0252662 A1 | 11/2006 | Soffin |
| 2006/0276357 A1 | 12/2006 | Smith, III et al. |
| 2006/0292104 A1 | 12/2006 | Guskey |
| 2007/0072781 A1 | 3/2007 | Soffin et al. |
| 2007/0110700 A1 | 5/2007 | Wells |
| 2007/0154402 A1 | 7/2007 | Trumbore et al. |
| 2007/0155637 A1 | 7/2007 | Smith, III et al. |
| 2007/0160555 A1 | 7/2007 | Staudigel |
| 2007/0179207 A1 | 8/2007 | Fernandez de Castro et al. |
| 2007/0225193 A1 | 9/2007 | Kuhlman et al. |
| 2007/0269397 A1 | 11/2007 | Terada |
| 2007/0292380 A1 | 12/2007 | Staudigel |
| 2008/0008668 A1 | 1/2008 | Harichian et al. |
| 2008/0019928 A1 | 1/2008 | Franzke |
| 2008/0063618 A1 | 3/2008 | Johnson |

(56) References Cited

U.S. PATENT DOCUMENTS

| | | |
|---|---|---|
| 2008/0096786 A1 | 4/2008 | Holt et al. |
| 2008/0138442 A1 | 6/2008 | Johnson |
| 2008/0152610 A1 | 6/2008 | Cajan |
| 2008/0160093 A1 | 7/2008 | Schwartz et al. |
| 2008/0206179 A1 | 8/2008 | Peffly et al. |
| 2008/0260655 A1 | 10/2008 | Tamarkin et al. |
| 2008/0260665 A1 | 10/2008 | Guerchet et al. |
| 2008/0261844 A1 | 10/2008 | Ruppert et al. |
| 2008/0317698 A1 | 12/2008 | Wells et al. |
| 2009/0029900 A1 | 1/2009 | Cetti et al. |
| 2009/0041702 A1 | 2/2009 | Molenda |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0197784 A1 | 8/2009 | Ainger |
| 2009/0221463 A1 | 9/2009 | Kitko et al. |
| 2009/0246236 A1 | 10/2009 | Kitko |
| 2009/0312224 A1 | 12/2009 | Yang et al. |
| 2009/0324505 A1 | 12/2009 | Seidling |
| 2010/0183539 A1 | 7/2010 | Bernhardt |
| 2010/0310644 A1 | 12/2010 | Liebmann |
| 2011/0008267 A1 | 1/2011 | Arkin et al. |
| 2011/0165107 A1 | 7/2011 | Derks et al. |
| 2011/0171155 A1 | 7/2011 | Federle |
| 2011/0232668 A1 | 9/2011 | Hoffmann et al. |
| 2011/0245126 A1 | 10/2011 | Tsaur et al. |
| 2011/0268778 A1 | 11/2011 | Dihora |
| 2011/0269657 A1 | 11/2011 | Dihora et al. |
| 2011/0305739 A1 | 12/2011 | Royce |
| 2011/0319790 A1 | 12/2011 | Kost et al. |
| 2012/0014901 A1 | 1/2012 | Sunkel et al. |
| 2012/0031419 A1 | 2/2012 | Batt |
| 2012/0034173 A1 | 2/2012 | Batt |
| 2012/0087883 A1 | 4/2012 | Leray et al. |
| 2012/0100091 A1 | 4/2012 | Hata et al. |
| 2012/0100092 A1 | 4/2012 | Murray |
| 2012/0291911 A1 | 11/2012 | Smith |
| 2012/0309660 A1 | 12/2012 | Kawasoe |
| 2012/0316095 A1 | 12/2012 | Wei et al. |
| 2013/0034515 A1 | 2/2013 | Stone et al. |
| 2013/0045285 A1 | 2/2013 | Stella et al. |
| 2013/0053295 A1 | 2/2013 | Kinoshita et al. |
| 2013/0053300 A1 | 2/2013 | Scheibel et al. |
| 2013/0089587 A1 | 4/2013 | Staudigel |
| 2013/0115173 A1 | 5/2013 | Trumbore et al. |
| 2013/0143784 A1 | 6/2013 | Rizk |
| 2013/0150338 A1 | 6/2013 | Ananthapadmanabhan |
| 2013/0156712 A1 | 6/2013 | Frantz |
| 2013/0189212 A1 | 7/2013 | Jawale et al. |
| 2013/0211952 A1 | 8/2013 | Sugaya |
| 2013/0216491 A1 | 8/2013 | Ogihara et al. |
| 2013/0243718 A1 | 9/2013 | Pasquet |
| 2013/0244922 A1 | 9/2013 | Bartelt |
| 2013/0251659 A1 | 9/2013 | Derks et al. |
| 2013/0280192 A1 | 10/2013 | Carter et al. |
| 2013/0280202 A1 | 10/2013 | Stella et al. |
| 2013/0284195 A1 | 10/2013 | Murdock |
| 2013/0296289 A1 | 11/2013 | Hall et al. |
| 2014/0037703 A1 | 2/2014 | Dihora et al. |
| 2014/0039066 A1 | 2/2014 | Grimadell et al. |
| 2014/0086893 A1 | 3/2014 | Gutmann et al. |
| 2014/0112879 A1 | 4/2014 | Molenda et al. |
| 2014/0127149 A1 | 5/2014 | Lepilleur |
| 2014/0131395 A1 | 5/2014 | Chang |
| 2014/0134125 A1 | 5/2014 | Dahl |
| 2014/0147025 A1 | 5/2014 | Periaswamy |
| 2014/0162979 A1 | 6/2014 | Palla-venkata |
| 2014/0171471 A1 | 6/2014 | Krueger |
| 2014/0216495 A1 | 8/2014 | Bureiko |
| 2014/0228268 A1 | 8/2014 | Fahl et al. |
| 2014/0237732 A1 | 8/2014 | Zuedel Fernandes et al. |
| 2014/0246515 A1 | 9/2014 | Nakajima |
| 2014/0308227 A1 | 10/2014 | Mabille |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2015/0021496 A1 | 1/2015 | Shabbir |
| 2015/0037273 A1 | 2/2015 | Wagner |
| 2015/0050231 A1 | 2/2015 | Murase |
| 2015/0071977 A1 | 3/2015 | Dihora |
| 2015/0093420 A1 | 4/2015 | Snyder |
| 2015/0093429 A1 | 4/2015 | Carter et al. |
| 2015/0098921 A1 | 4/2015 | Franzke et al. |
| 2015/0099684 A1 | 4/2015 | Boutique |
| 2015/0110728 A1 | 4/2015 | Jayaswal |
| 2015/0147286 A1 | 5/2015 | Barrera |
| 2015/0218496 A1 | 8/2015 | Schmiedel et al. |
| 2015/0262354 A1 | 9/2015 | Periaswamy |
| 2015/0297489 A1 | 10/2015 | Kleinen |
| 2015/0299400 A1 | 10/2015 | Wagner et al. |
| 2015/0313818 A1 | 11/2015 | Stagg |
| 2015/0359725 A1 | 12/2015 | Glenn, Jr. et al. |
| 2015/0359726 A1 | 12/2015 | Glenn, Jr. et al. |
| 2015/0359728 A1 | 12/2015 | Glenn, Jr. et al. |
| 2016/0008257 A1 | 1/2016 | Zhou et al. |
| 2016/0022566 A1 | 1/2016 | Figura |
| 2016/0113849 A1 | 4/2016 | Grimadell et al. |
| 2016/0128944 A1 | 5/2016 | Chawrai |
| 2016/0193125 A1 | 7/2016 | Jones et al. |
| 2016/0235643 A1 | 8/2016 | Mathonneau et al. |
| 2016/0250137 A1 | 9/2016 | Noor et al. |
| 2016/0279048 A1 | 9/2016 | Jayaswal et al. |
| 2016/0287503 A1 | 10/2016 | Schroeder |
| 2016/0287509 A1 | 10/2016 | Peffly |
| 2016/0303043 A1 | 10/2016 | Khoury |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310371 A1 | 10/2016 | Zhao |
| 2016/0310375 A1 | 10/2016 | Torres Rivera |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |
| 2016/0317424 A1 | 11/2016 | Kadir |
| 2016/0354300 A1 | 12/2016 | Thompson et al. |
| 2017/0071837 A1 | 3/2017 | Schelges et al. |
| 2017/0101609 A1 | 4/2017 | Vargas |
| 2017/0110690 A1 | 4/2017 | Lamansky et al. |
| 2017/0110695 A1 | 4/2017 | Nishikawa et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0239155 A1 | 8/2017 | Hartnett |
| 2017/0252273 A1 | 9/2017 | Renock et al. |
| 2017/0278249 A1 | 9/2017 | Stofel et al. |
| 2017/0283959 A1 | 10/2017 | Shellef |
| 2017/0304172 A1 | 10/2017 | Chang et al. |
| 2017/0304184 A1 | 10/2017 | Glenn, Jr. |
| 2017/0304185 A1 | 10/2017 | Glenn, Jr. et al. |
| 2017/0304186 A1 | 10/2017 | Glenn, Jr. |
| 2017/0333321 A1 | 11/2017 | Carnali |
| 2018/0044097 A1 | 2/2018 | Zeik |
| 2018/0057451 A1 | 3/2018 | Owens et al. |
| 2018/0110594 A1 | 4/2018 | Atkin |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera et al. |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson et al. |
| 2018/0110696 A1 | 4/2018 | Johnson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | Park et al. |
| 2018/0116941 A1 | 5/2018 | Wang |

(56) References Cited

U.S. PATENT DOCUMENTS

| | | |
|---|---|---|
| 2018/0221266 A1 | 8/2018 | Zhao et al. |
| 2018/0256481 A1 | 9/2018 | Glenn, Jr. |
| 2018/0311135 A1 | 11/2018 | Chang |
| 2018/0311136 A1 | 11/2018 | Chang |
| 2018/0318194 A1 | 11/2018 | Hoffmann et al. |
| 2018/0344611 A1 | 12/2018 | Zhao et al. |
| 2018/0344612 A1 | 12/2018 | Zhao et al. |
| 2018/0344613 A1 | 12/2018 | Zhao et al. |
| 2018/0344614 A1 | 12/2018 | Zhao et al. |
| 2019/0105242 A1 | 4/2019 | Song |
| 2019/0105243 A1 | 4/2019 | Song |
| 2019/0105244 A1 | 4/2019 | Song |
| 2019/0105245 A1 | 4/2019 | Song |
| 2019/0105246 A1 | 4/2019 | Cochran |
| 2019/0105247 A1 | 4/2019 | Song |
| 2019/0117543 A1 | 4/2019 | Zhao |
| 2019/0117544 A1 | 4/2019 | Zhao |
| 2019/0117545 A1 | 4/2019 | Zhao |
| 2019/0142711 A1 | 5/2019 | Torres Rivera |
| 2019/0167554 A1 | 6/2019 | Wankhade |
| 2019/0183777 A1 | 6/2019 | Gillis |
| 2019/0183778 A1 | 6/2019 | Glenn, Jr |
| 2019/0192405 A1 | 6/2019 | Zhao |
| 2019/0240121 A1 | 8/2019 | Torres Rivera |
| 2019/0307298 A1 | 10/2019 | Zhao |
| 2019/0365633 A1 | 12/2019 | Glenn, Jr. |
| 2020/0129402 A1 | 4/2020 | Jamadagni |
| 2020/0163846 A1 | 5/2020 | Song |
| 2020/0237628 A1 | 7/2020 | Torres Rivera |
| 2021/0022986 A1 | 1/2021 | Glenn, Jr. |

FOREIGN PATENT DOCUMENTS

| | | |
|---|---|---|
| CN | 102895151 A | 1/2013 |
| CN | 102697668 B | 8/2013 |
| CN | 103356408 A | 10/2013 |
| CN | 102697670 B | 7/2014 |
| CN | 102851015 B | 12/2014 |
| CN | 105007884 A | 10/2015 |
| CN | 105726393 A | 7/2016 |
| CN | 105769617 A | 7/2016 |
| CN | 106750361 A | 5/2017 |
| DE | 4315396 A1 | 11/1994 |
| DE | 202005009618 U1 | 9/2005 |
| DE | 102008050430 A1 | 4/2010 |
| DE | 102015204987 A1 | 9/2016 |
| EP | 0574086 A2 | 12/1993 |
| EP | 0674898 A2 | 10/1995 |
| EP | 1340485 A2 | 2/2003 |
| EP | 1346720 A2 | 9/2003 |
| EP | 067898 B2 | 3/2006 |
| EP | 1714678 A1 | 10/2006 |
| EP | 2042216 B1 | 9/2015 |
| JP | S56011009 A | 12/1981 |
| JP | 58113300 | 7/1983 |
| JP | S58113300 A | 7/1983 |
| JP | S61236708 A | 10/1986 |
| JP | H04364114 A | 12/1992 |
| JP | 07252134 A | 10/1995 |
| JP | H08310924 A | 11/1996 |
| JP | 09030938 A | 2/1997 |
| JP | H09175961 A | 7/1997 |
| JP | 2964226 B2 | 10/1999 |
| JP | 3069802 B2 | 7/2000 |
| JP | 2003201217 A | 12/2001 |
| JP | 2002179552 A | 6/2002 |
| JP | 2002226889 A | 8/2002 |
| JP | 2003055699 A | 2/2003 |
| JP | 3480165 B2 | 12/2003 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 2005232113 A | 9/2005 |
| JP | 2006124312 A | 5/2006 |
| JP | 2006183039 A | 7/2006 |
| JP | 2006193549 A | 7/2006 |
| JP | 2007131687 A | 5/2007 |
| JP | 2008001626 A | 1/2008 |
| JP | 2008214292 A | 9/2008 |
| JP | 2009096778 A | 5/2009 |
| JP | 2011153167 A | 8/2011 |
| JP | 2011190221 A | 9/2011 |
| JP | 5041113 B2 | 7/2012 |
| JP | 2013010757 A | 1/2013 |
| JP | 2013091641 A | 5/2013 |
| JP | 2013151434 A | 8/2013 |
| JP | 6046394 B2 | 1/2014 |
| JP | 2014024875 A | 2/2014 |
| JP | 2014091723 A | 5/2014 |
| JP | 5667790 B2 | 2/2015 |
| JP | 2015101545 A | 6/2015 |
| JP | 2018012673 A | 1/2018 |
| KR | 20050031235 A | 4/2005 |
| KR | 1020080111280 | 12/2008 |
| KR | 20140060882 A | 5/2014 |
| WO | 9114759 A1 | 10/1991 |
| WO | 91017237 A1 | 11/1991 |
| WO | WO199325650 A1 | 12/1993 |
| WO | WO9502389 A1 | 1/1995 |
| WO | WO9726854 A1 | 7/1997 |
| WO | WO9823258 A1 | 6/1998 |
| WO | WO9918928 A1 | 4/1999 |
| WO | 9924013 A1 | 5/1999 |
| WO | WO9924004 A1 | 5/1999 |
| WO | 0012553 A1 | 3/2000 |
| WO | WO0142409 A1 | 6/2001 |
| WO | WO0148021 A1 | 7/2001 |
| WO | 2004078901 A1 | 9/2004 |
| WO | WO2005023975 A1 | 3/2005 |
| WO | 2008145582 A1 | 12/2008 |
| WO | WO2009016555 A1 | 2/2009 |
| WO | WO2010052147 A2 | 5/2010 |
| WO | 2012017091 A2 | 2/2012 |
| WO | WO2012055587 A1 | 5/2012 |
| WO | WO2012084970 A1 | 6/2012 |
| WO | WO2013010706 A1 | 1/2013 |
| WO | 2014073245 A1 | 5/2014 |
| WO | WO2014148245 A1 | 9/2014 |
| WO | 2015122371 A1 | 8/2015 |
| WO | WO2016147196 A1 | 9/2016 |
| WO | 2017052161 A1 | 3/2017 |
| WO | WO2017140798 A1 | 8/2017 |
| WO | WO2017207685 A1 | 12/2017 |
| WO | WO2018023180 A1 | 2/2018 |

OTHER PUBLICATIONS

All Final and Non-Final Office Actions for U.S. Appl. No. 15/135,701.
All Final and Non-Final Office Actions for U.S. Appl. No. 15/135,998.
All Final and Non-Final Office Actions for U.S. Appl. No. 15/145,696.
All Final and Non-Final Office Actions for U.S. Appl. No. 15/2788,938.
All Final and Non-Final Office Actions for U.S. Appl. No. 15/299,860.
All final and non-final office actions for U.S. Appl. No. 15/379,660.
All final and non-final office actions for U.S. Appl. No. 15/379,674.
All final and non-final office actions for U.S. Appl. No. 15/448,911.
All final and non-final office actions for U.S. Appl. No. 15/467,317.
All Final and Non-Final Office Actions for U.S. Appl. No. 15/481,777.
All Final and Non-Final Office Actions for U.S. Appl. No. 15/788,895.
All Final and Non-Final Office Actions for U.S. Appl. No. 15/788,949.
All Final and Non-Final Office Actions for U.S. Appl. No. 15/788,998.
All Final and Non-Final Office Actions for U.S. Appl. No. 15/789,010.
All Final and Non-Final Office Actions for U.S. Appl. No. 15/789,020.
All Final and Non-Final Office Actions for U.S. Appl. No. 15/789,030.
All Final and Non-Final Office Actions for U.S. Appl. No. 15/789,038.
All Final and Non-Final Office Actions for U.S. Appl. No. 15/789,044.
All Final and Non-Final Office Actions for U.S. Appl. No. 15/789,081.
All Final and Non-Final Office Actions for U.S. Appl. No. 15/789,172.
All Final and Non-Final Office Actions for U.S. Appl. No. 15/789,188.
All Final and Non-Final Office Actions for U.S. Appl. No. 15/789,208.
All Final and Non-final Office Actions for U.S. Appl. No. 15/923,499.
All final and non-final office actions for U.S. Appl. No. 15/962,327.

(56) References Cited

OTHER PUBLICATIONS

All final and non-final office actions for U.S. Appl. No. 15/962,351.
All final and non-final office actions for U.S. Appl. No. 16/001,045.
All final and non-final office actions for U.S. Appl. No. 16/001,053.
All final and non-final office actions for U.S. Appl. No. 16/001,058.
All final and non-final office actions for U.S. Appl. No. 16/001,064.
All Final and Non-Final Office Actions for U.S. Appl. No. 16/156,015.
All Final and Non-Final Office Actions for U.S. Appl. No. 16/156,038.
All Final and Non-Final Office Actions for U.S. Appl. No. 16/156,053.
All Final and Non-Final Office Actions for U.S. Appl. No. 16/156,066.
All Final and Non-Final Office Actions for U.S. Appl. No. 16/156,072.
All final and non-final office actions for U.S. Appl. No. 16/165,016.
All final and non-final office actions for U.S. Appl. No. 16/165,033.
All final and non-final office actions for U.S. Appl. No. 16/165,044.
All final and non-final office actions for U.S. Appl. No. 16/170,516.
All final and non-final office actions for U.S. Appl. No. 16/170,711.
All final and non-final office actions for U.S. Appl. No. 16/226,914.
All final and non-final office actions for U.S. Appl. No. 16/226,927.
All final and non-final office actions for U.S. Appl. No. 16/248,900.
All final and non-final office actions for U.S. Appl. No. 16/285,535.
All final and non-final office actions for U.S. Appl. No. 16/376,033.
All final and non-final office actions for U.S. Appl. No. 16/390,270.
All final and non-final office actions for U.S. Appl. No. 16/532,556.
Anonymous: "MERQUAT Polyquaternium 47 Series, Water Soluble Polymers for Personal Care", Jul. 30, 2017, URL: https://www.in-cosmetics.com/_novadocuments/2729, retrieved on Dec. 21, 2018.
Carbopol Aqua SF-1 Polymer Technical Data Sheet, TDS-294, Dec. 2000.
Christensen et al., "Experimental Determination of Bubble Size Distribution in a Water Column by Interferometric Particle Imaging and Telecentric Direct Image Method", Student Report, Aalborg University, Jun. 3, 2014.
Dehyquart Guar: Published Nov. 2010.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018, p. 1.
PCT International Search Report and Written Opinion for PCT/US2016/028728 dated Aug. 5, 2016.
PCT International Search Report and Written Opinion for PCT/US2016/028729 dated Jun. 15, 2016.
PCT International Search Report and Written Opinion for PCT/US2016/028730 dated Aug. 5, 2016.
PCT International Search Report and Written Opinion for PCT/US2016/028735 dated Jul. 25, 2016.
PCT International Search Report and Written Opinion for PCT/US2016/028736 dated Jul. 25, 2016.
PCT International Search Report and Written Opinion for PCT/US2016/028742 dated Jul. 18, 2016.
PCT International Search Report and Written Opinion for PCT/US2016/058123 dated Dec. 21, 2016.
PCT International Search Report and Written Opinion for PCT/US2016/066752 dated Feb. 22, 2017.
PCT International Search Report and Written Opinion for PCT/US2016/066757 dated Feb. 22, 2017.
PCT International Search Report and Written Opinion for PCT/US2017/020604 dated May 11, 2017.
PCT International Search Report and Written Opinion for PCT/US2017/022737 dated Jun. 22, 2017.
PCT International Search Report and Written Opinion for PCT/US2017/057486 dated Jan. 9, 2018.
PCT International Search Report and Written Opinion for PCT/US2017/057487 dated Dec. 19, 2017.
PCT International Search Report and Written Opinion for PCT/US2017/057488 dated Dec. 12, 2017.
PCT International Search Report and Written Opinion for PCT/US2017/057497 dated Jan. 8, 2018.
PCT International Search Report and Written Opinion for PCT/US2017/057503 dated Dec. 13, 2017.
PCT International Search Report and Written Opinion for PCT/US2017/057507 dated Dec. 13, 2017.
PCT International Search Report and Written Opinion for PCT/US2017/057510 dated Jan. 11, 2018.
PCT International Search Report and Written Opinion for PCT/US2017/057511 dated Feb. 2, 2018.
PCT International Search Report and Written Opinion for PCT/US2017/057514 dated Jan. 10, 2018.
PCT International Search Report and Written Opinion for PCT/US2017/057515 dated Dec. 11, 2017.
PCT International Search Report and Written Opinion for PCT/US2017/057522 dated Feb. 2, 2018.
PCT International Search Report and Written Opinion for PCT/US2017/057533 dated Jan. 8, 2018.
PCT International Search Report and Written Opinion for PCT/US2017/057541 dated Dec. 22, 2017.
PCT International Search Report and Written Opinion for PCT/US2018/029313 dated Jul. 11, 2018.
PCT International Search Report and Written Opinion for PCT/US2018/029315 dated Jun. 27, 2018.
PCT International Search Report and Written Opinion for PCT/US2018/036181 dated Aug. 3, 2018.
PCT International Search Report and Written Opinion for PCT/US2018/036185 dated Aug. 3, 2018.
PCT International Search Report and Written Opinion for PCT/US2018/055102 dated Jan. 9, 2019.
PCT International Search Report and Written Opinion for PCT/US2018/055103 dated Jan. 9, 2019.
PCT International Search Report and Written Opinion for PCT/US2018/055104 dated Jan. 18, 2019.
PCT International Search Report and Written Opinion for PCT/US2018/055105 dated Jan. 8, 2019.
PCT International Search Report and Written Opinion for PCT/US2018/055106 dated Jan. 16, 2019.
PCT International Search Report and Written Opinion for PCT/US2018/055107 dated Jan. 28, 2019.
PCT International Search Report and Written Opinion for PCT/US2018/056669 dated Jan. 31, 2019.
PCT International Search Report and Written Opinion for PCT/US2018/056673 dated Feb. 5, 2019.
PCT International Search Report and Written Opinion for PCT/US2018/056674 dated Feb. 5, 2019.
PCT International Search Report and Written Opinion for PCT/US2018/057451 dated Feb. 25, 2019.
PCT International Search Report and Written Opinion for PCT/US2018/057476 dated Jan. 18, 2019.
PCT International Search Report and Written Opinion for PCT/US2018/066697 dated Mar. 15, 2019.
PCT International Search Report and Written Opinion for PCT/US2018/066701 dated Mar. 15, 2019.
PCT International Search Report and Written Opinion for PCT/US2019/025923 dated Jun. 24, 2019.
PCT International Search Report and Written Opinion for PCT/US2019/057974 dated Feb. 3, 2020.
Polyquaternium: "Final Report on the Safety Assessment of the Polyquatemium-10", Journal of the American College of Toxicology, Jan. 1, 1988, URL: http://www.beauty-review.nl/wp-content/uploads/2015/02/Final-Report-on-the Safety-Assessment-of-Polyquaternium-10.pdf, retrieved on Dec. 20, 2018.
Practical Modem Hair Science, Published 2012.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, Nov. 1, 2008, pp. 304-308, p. 305—left-hand column.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012.
"Deep Image Matting", Ning Xu et al, Beckman Institute for Advanced Science and Technology, University of Illinois at Urbana-Champaign, Adobe Research, Mar. 10, 2017.
All final and non-final office actions for U.S. Appl. No. 16/846,594.

(56) References Cited

OTHER PUBLICATIONS

D'Souza et al., Shampoo and Conditioners: What a Dermatologist Should Know? Indian J Dermatol, May-Jun. 2015 60(3), 248-254 (2015).

Inspection cerlilicate for Hostapon® CCG, Clariant Ibérica Production, S.A., May 6, 2019.

Musazzi, "Emulsion versus nonoemulsion: how much is the formulative shift critical for a cosmetic product?" (Drug Deliv. and Trans. Res. (2018) 8:414-421 (Year: 2018).

Product Bulletin, Amphosol® CG, Cocamidopropyl Betaine, Stepan Company, Jun. 2011.

Product Data Sheet for Chemoryl™LS Surfactant, Sodium Lauroyl Sarcosinate, Lubrizol Advanced Materials, Inc., Mar. 24, 2020.

Product Data Sheet, Eversoft™ UCS-40S, Disodium Cocoyl Glutamate (Sodium Cocoyl Glutamate*), Sino Lion USA, Jul. 2018.

Product Fact Sheet—Hostapon® CCG, mild anionic surfactant for the cosmetic industry, Clariant International Ltd., Aug. 2014.

Product Fact Sheet, Hostapon® CGN, Mild anionic surfactant for the cosmetic industry, Clariant International Ltd., Jan. 2016.

UL Prospector® Product Data Sheet, Plantacare® 818 UP, C8-16 fatty alcohol glucoside, BASF, May 21, 2015.

All final and non-final office actions for U.S. Appl. No. 17/071,033.

Fevola, Michael J. "Guar Hydroxypropyltrimonium Chloride." Cosmetics and toiletries 127.1 (2012) 16-21.

Medvedev, Diffusion Coefficients in Multicomponent Mixtures, PhD Thesis from Technical University of Denmark, 2005, 181 pages.

Perm Inc, , Diffusion Coefficient: Measurement Techiques, https://perminc.com/resources/fundamentals-of-fluid-flow-in-porous-media/chapter-3-molecular-diffusion/diffusion-coefficient/measurement-techniques, Oct. 2020.

Robinson et al., Final Report of the Amended Safety Assessment of Sodium Laureth Sulfate and Related Salts of SulfatedEthoxylated Alcohols, International Journal of Toxicology 29(Supplement 3) 151S-161S, 2010 (Year: 2010).

"Anti-Dandruff Shampoo", Mintel Database, Record No. 752198, dated Aug. 2007 ; pp. 1-3.

"Dandruff Control Shampoo", Mintel Database, Record No. 2300131, dated Jan. 2014; pp. 1-2.

Parchem fine & specialty chemicals. MIPA-laureth sulfate supplier distributor—CAS 83016-76-6; dated 2021; pp. 1-7.

Schwartz et al. ("Shampoos for Normal Scalp Hygiene and Dandruff." Cosmetic Dermatology. Oxford, UK: Wiley-Blackwell, 2010.115-122. Web). (Year: 2010) 1pg.

|  | Example 3 | Example 9 | Example 18 | Example 19 |
|---|---|---|---|---|
| Key measures | A | B | C | D |
| Base total responses (n=) | 197 | 176 | 186 | 174 |
| Overall Clean | 81 | 80 | 82 D | 77 |
| Overall Hair and Scalp feeling clean for a long time | 77 D | 73 | 75 | 70 |
| Overall mildness on hair and scalp | 80 | 79 | 80 | 79 |
|  |  |  |  |  |
| Application, Lathering, Rinsing |  |  |  |  |
| Being easy to spread | 84 | 81 | 81 | 80 |
| Being easy to rinse | 83 | 84 | 85 | 81 |
|  |  |  |  |  |
| After Rinsing Shampoo |  |  |  |  |
| Leaving my scalp feeling clean after rinsing shampoo | 81 D | 78 | 80 | 76 |
| Leaving my roots hair feeling clean after rinsing shampoo | 81 B,D | 76 | 79 | 74 |
| Leaving my scalp and hair feeling without unwanted residue after rinsing shampoo | 81 D | 81 D | 82 D | 76 |
| Easy to run fingers / combs through hair rinsing shampoo | 76 | 72 | 74 | 71 |
|  |  |  |  |  |
| After Showering / washing |  |  |  |  |
| Leaving my scalp feeling clean when damp after showing | 82 B,D | 78 | 81 D | 75 |
| Leaving my roots feeling clean when damp after showing | 81 B,D | 77 | 80 D | 75 |
| Easy to run fingers/comb through damp hair after showing | 75 | 73 | 76 | 72 |

LOW SURFACTANT AEROSOL ANTIDANDRUFF COMPOSITION

FIELD OF THE INVENTION

The present invention relates to an aerosol antidandruff composition with a low surfactant concentration which is providing deposition of actives and an improved hair feel while maintaining composition efficacy.

BACKGROUND OF THE INVENTION

For years, anti-dandruff shampoos have been widely used to treat dandruff and clean hair and scalp, but there still remains a need for improved anti-dandruff shampoos. In general, anti-dandruff shampoos are formulated with anti-dandruff agents in combination with surfactants and aqueous systems that are intended to deposit the anti-dandruff agents on the scalp. The anti-dandruff agents can be insoluble particulates such as zinc pyrithione and/or surfactant soluble substances such as climbazole or piroctone olamine. An important aspect of the anti-dandruff shampoos is its ability to enable sufficient deposition of the anti-dandruff agent on the scalp. This is particularly challenging in the case of surfactant soluble anti-dandruff agents where it can prove difficult to deposit on scalp much more than 1-2% of the quantity of the agent that is present in the product, while the remaining 98-99% of the soluble agent in the formulas is rinsed away. As many of the anti-dandruff agents can be relatively expensive, allowing more than 97% of the soluble agents to rinse away is equivalent to pouring money down the drain. Thus, there remains a need for a shampoo that can more efficiently deposit soluble anti-dandruff agents. Also, as consumers continue to desire a shampoo that delivers superior anti-dandruff efficacy, there remains a need for a shampoo that can deposit on scalp a higher percentage of the soluble agents present in anti-dandruff shampoos.

The present invention has surprisingly found that shampoos that comprise relatively low surfactant concentrations that are delivered in a foam form can deliver increased quantities of surfactant soluble anti-dandruff agents on the scalp. The low surfactant content of such shampoo compositions come with additional benefits. It is well known that low surfactant compositions provide milder cleansing with less skin irritation and stripping of the hair fibers. The inventive compositions rinse faster, but they still provide (a) good wet feel and combability and (b) high ability to remove sebum.

Without being bound by theory, the observation of improved deposition of the anti-dandruff active on scalp observed by the low-surfactant shampoo composition that is delivered as an aerosol foam may be related to the use of a propellant in the composition. More specifically, the presence of a propellant in the shampoo composition may contribute to making the active less soluble in the shampoo as the propellant is likely to be partially or totally residing in surfactant micelles. As a result, the solubility of the anti-dandruff will be reduced or, in other words, the saturation concentration of the anti-dandruff active will be reduced, and the active will have the tendency to precipitate as a water insoluble material on the scalp as the propellant and the aqueous carrier evaporate.

SUMMARY OF THE INVENTION

The present invention is directed to a foaming composition comprising from about 5% to about 13% total surfactant of one or more anionic surfactants; from 0.1% to about 2% of a surfactant soluble antidandruff active; from about 3% to about 15% of a blowing agent, wherein the foaming composition is at a pH of about 3.5 to 6.5

BRIEF DESCRIPTION OF THE DRAWINGS

FIG. 1 show that for key attributes of the low surfactant foam shampoos examples 9, and 19 show parity "overall clean" response vs. high surfactant foam shampoo Example 3. Example 18 which contains PEG23M and low surfactant shows that it is directionally higher than all foams and significantly higher than the Example 19 which contains silicone which could make the consumers scalp/hair feel oily greasy.

FIG. 1 contains the formula details per leg.

The patent or application file contains at least one drawing executed in color. Copies of this patent or patent application publication with color drawings will be provided by the Office upon request and payment of the necessary fee.

DETAILED DESCRIPTION OF THE INVENTION

While the specification concludes with claims particularly pointing out and distinctly claiming the invention, it is believed that the present invention will be better understood from the following description.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

As used herein, "personal care compositions" includes products such as shampoos, shower gels, liquid hand cleansers, hair colorants, facial cleansers, and other surfactant-based liquid compositions As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations are expressly written herein. Every minimum numerical limitation given throughout this specification will include every higher numerical limitation, as if such higher numerical limitations are expressly written herein. Every numerical range given throughout this specification are include every narrower numerical range that falls within such broader numerical range, as if such narrower numerical ranges are all expressly written herein.

Detersive Surfactant

The hair care composition may comprise greater than about 20% by weight of a surfactant system which provides cleaning performance to the composition. The surfactant system comprises an anionic surfactant and/or a combination of anionic surfactants, with a co-surfactant selected from the group consisting of amphoteric, zwitterionic, non-ionic and mixtures thereof. Various examples and descriptions of detersive surfactants are set forth in U.S. Pat. No. 8,440,605; U.S. Patent Application Publication No. 2009/155383; and U.S. Patent Application Publication No. 2009/0221463, which are incorporated herein by reference in their entirety.

The hair care composition may comprise from about 18% to about 36%, from about 20% to about 32%, and/or from about 22% to about 28% by weight of one or more anionic surfactants.

The composition of the present invention can also include anionic surfactants selected from the group consisting of:
a) $R_1 O(CH_2CHR_3O)_y SO_3M$;
b) $CH_3 (CH_2)_z CHR_2 CH_2 O (CH_2 CHR_3O)_y SO_3M$; and
c) mixtures thereof, where $R_1$ represents $CH_3 (CH_2)_{10}$, $R_2$ represents H or a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not zero (0), and M is a monovalent or divalent, positively-charged cation.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the hair care composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, undecyl sulfate and combinations thereof. The anionic surfactant may be sodium lauryl sulfate or sodium laureth sulfate.

Suitable anionic alkyl sulfates and alkyl ether sulfate surfactants include, but are not limited to, those having branched alkyl chains which are synthesized from C8 to C18 2-alkylbranched alcohols which may be selected from the group consisting of: Guerbet alcohols, aldol alcohols, oxo alcohols and mixtures thereof. Nonlimiting examples of the 2-alkyl branched alcohols include the Guerbet alcohols such as 2-methyl-1-undecanol, 2-ethyl-1-decanol, 2-methyl-1-dodecanol, 2-butyl 1-octanol, 2-butyl-1-nonanol, 2-ethyl-1-undecanol, 2-propyl-1-nonanol, 2-pentyl-1-octanol, 2-pentyl-1-heptanol, and those sold under the tradename ISOFOL® (Sasol), and oxo alcohols, e.g., those sold under the tradenames LIAL® (Sasol), ISALCHEM® (Sasol), NEODOL® (Shell), The hair care composition may comprise a co-surfactant. The co-surfactant can be selected from the group consisting of amphoteric surfactant, zwitterionic surfactant, non-ionic surfactant and mixtures thereof. The co-surfactant can include, but is not limited to, lauramidopropyl betaine, cocoamidopropyl betaine, lauryl hydroxysultaine, sodium lauroamphoacetate, coco monoethanolamide and mixtures thereof.

The hair care composition may further comprise from about 1% to about 5%, from about 2% to about 4%, from about 2.5 to about 3% by weight of one or more amphoteric/zwitterionic, nonionic co-surfactants, or a mixture thereof.

Suitable amphoteric or zwitterionic surfactants for use in the hair care composition herein include those which are known for use in shampoo or other hair care cleansing. Non limiting examples of suitable zwitterionic or amphoteric surfactants are described in U.S. Pat. Nos. 5,104,646 and 5,106,609, which are incorporated herein by reference in their entirety.

Amphoteric co-surfactants suitable for use in the composition include those surfactants described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable amphoteric surfactant include, but are not limited to, those selected from the group consisting of: sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium auroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof The amphoteric co-surfactant can be a surfactant according to the following structure:

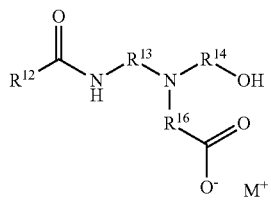

wherein R12 is a C-linked monovalent substituent selected from the group consisting of substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; R13, R14, and R15 are each independently selected from the group consisting of C-linked divalent straight alkyl systems comprising 1 to 3 carbon atoms, and C-linked divalent branched alkyl systems comprising 1 to 3 carbon atoms; and M+ is a monovalent counterion selected from the group consisting of sodium, ammonium and protonated triethanolamine. The amphoteric surfactant may be selected from the group consisting of: sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, triethanolamine cocoamphoacetate, and mixtures thereof.

The composition may comprises a zwitterionic co-surfactant, wherein the zwitterionic surfactant is a derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant can be selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. A suitable zwitterionic surfactant is lauryl hydroxysultaine. The zwitterionic surfactant can be selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

The co-surfactant can be a zwitterionic surfactant, wherein the zwitterionic surfactant is selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

The co-surfactant can be a non-ionic surfactant selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, and mixtures thereof.

Non limiting examples of other anionic, zwitterionic, amphoteric, and non-ionic additional surfactants suitable for use in the hair care composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

Non Sulfate Surfactants

Suitable surfactants that are substantially free of sulfates can include isethionates, sulfonates, sulfosuccinates, sulfoacetates, acyl glucosides, acyl glycinates, acyl sarcosinare, acyl glutamates, acyl alaninates, alkyl glucosides, alkyl polyglucosides, acyl glucosides, glucamides, glucose carboxylates, amphoacetates, taurates, other acyl aminoacids, betaines, sultaines, and/or phosphate esters. Suitable surfactants that are substantially free of sulfates can contain carboxylic acids.

Viscosity Reducing Agent

The hair care composition may comprise from about 1% to about 5%, alternatively from about 2% to about 4%, alternatively from about 1% to about 3%, of one or more viscosity reducing agents, by weight of the hair care composition.

The viscosity reducing agents may be selected from the group consisting of The viscosity reducing agents may be selected from the group consisting of, ethanol, dipropylene glycol, sodium xylene sulfonate, alkoxylated silicone/ethoxylated silicone/propoxylated silicone/polyoxyethylene silicone/polyoxypropylene silicone/polyethyleneglycol silicone/PEG-8 silicone/PEG-9 silicone/PEG-n silicone/silicone ether (n could be another integer), non-limiting examples include PEG8-dimethicone A208) MW 855, PEG 8 Dimethicone D208 MW2706, Silsurf and combinations thereof.

The hair care composition described herein may have a liquid phase viscosity (composition prior to addition of the propellant) of from about 8 centipoise to about 25,000 centipoise, alternatively from about 9 centipoise to about 15,000 centipoise, alternatively from about 10 centipoise to about 11,000 centipoise, from about 100 centipoise to about 3,000 centipoise. Further the viscosity measured at 25 C may be less than 3,000 centipoise. The concentrated hair composition viscosity values may be measured using a TA Instruments AR-G2 Rheometer with a concentric cylinder attachment at a shear rate of 2 reciprocal seconds at 25° C. In the present invention, a hair care composition may have a viscosity in a range that allows for ease of dispensing from a package configuration.

Water Miscible Solvents

The compositions can include water miscible glycols and other diols. Non-limiting examples include dipropylene glycol, tripropylene glycol, diethylene glycol, ethylene glycol, propylene glycol, 1,3-propane diol, 2,2-propanediol, 1,2-butanediol, 1,3-butanediol, 1,4-butanediol, 2,3-butanediol, 1-Propene, 1,3,3,3 Tetrafluoro-(1E), and 2-methyl-2,4-pentanediol.

Soluble Anti-Dandruff Agent

Anti-dandruff agent may be one material or a mixture selected from the groups consisting of: azoles, such as climbazole, ketoconazole, itraconazole, econazole, and elubiol; hydroxy pyridones, such as octopirox (piroctone olamine), hydroxyl pyridones, N-Hydroxy-6-octyloxypyridine-2(1H)one, hexamidine diisethionate, ciclopirox, rilopirox, and MEA-Hydroxyoctyloxypyridinone; kerolytic agents, such as salicylic acid and other hydroxy acids; strobilurins such as azoxystrobin and metal chelators such as 1,10-phenanthroline.

In the present invention, the azole anti-microbials may be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. The azole anti-microbial agent may be ketoconazole.

The soluble anti-dandruff agent may be present in an amount from about 0.01% to about 10%, from about 0.1% to about 2%, and from 0.6% to about 1% and from about 0.5% to about 0.8%. The soluble antidandruff agent can be surfactant soluble and thus surfactant soluble antidandruff agents.

Cationic Polymers

The hair care composition also comprises a cationic polymer. These cationic polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic polymer can be a mixture of cationic polymers.

The hair care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

The cationic polymer, including but not limited to a cationic guar polymer, may have a molecular weight of less than 1.0 million g/mol, or from about 10 thousand to about 1 million g/mol, or from about 25 thousand to about 1 million g/mol, or from about 50 thousand to about 1 million g/mol, or from about 100 thousand to about 1 million g/mol.

The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.7 meq/g.

The cationic guar polymer may have a weight average molecular weight of less than about 1.0 million g/mol, and has a charge density of from about 0.1 meq/g to about 2.5 meq/g. The cationic guar polymer may have a weight average molecular weight of less than 950 thousand g/mol, or from about 10 thousand to about 900 thousand g/mol, or from about 25 thousand to about 900 thousand g/mol, or from about 50 thousand to about 900 thousand g/mol, or from about 100 thousand to about 900 thousand g/mol. from about 150 thousand to about 800 thousand g/mol. The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.5 meq/g.

The hair care composition can comprise from about 0.05% to less than about 1%, from about 0.05% to about 0.9%, from about 0.1% to about 0.8%, or from about 0.2% to about 0.7% of cationic polymer (a), by total weight of the composition.

The cationic guar polymer may be formed from quaternary ammonium compounds. The quaternary ammonium compounds for forming the cationic guar polymer may conform to the general formula 1:

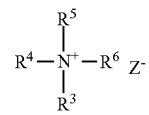

wherein where $R^3$, $R^4$ and $R^5$ are methyl or ethyl groups; $R^6$ is either an epoxyalkyl group of the general formula 2:

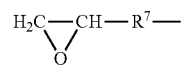

or $R^6$ is a halohydrin group of the general formula 3:

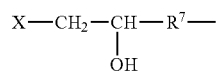

wherein $R^7$ is a $C_1$ to $C_3$ alkylene; X is chlorine or bromine, and Z is an anion such as Cl—, Br—, I— or $HSO_4$—.

In an embodiment, the cationic guar polymer conforms to the general formula 4:

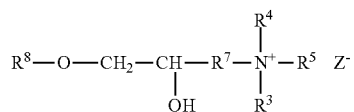

wherein $R^8$ is guar gum; and wherein $R^4$, $R^5$, $R^6$ and $R^7$ are as defined above; and wherein Z is a halogen. In an embodiment, the cationic guar polymer conforms to Formula 5:

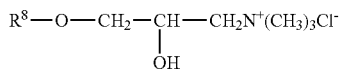

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a molecular weight of 500,000 g/mol. Other suitable guar hydroxypropyltrimonium chloride are: guar hydroxypropyltrimonium chloride which has a charge density of about 1.1 meq/g and a molecular weight of about 500,000 g/mol is available from ASI, a charge density of about 1.5 meq/g and a molecular weight of about 500,000 g/mole is available from ASI. Other suitable guar hydroxypropyltrimonium chloride are: Hi-Care 1000, which has a charge density of about 0.7 meq/g and a Molecular weight of about 600,000 g/mole and is available from Rhodia; N-Hance 3269 and N-Hance 3270, which has a charge density of about 0.7 meq/g and a molecular weight of about 425,000 g/mol and is available from ASIAquaCat CG518 has a charge density of about 0.9 meq/g and a Molecular weight of about 50,000 g/mol and is available from ASI. BF-13, which is a borate (boron) free guar of charge density of about 1.1 meq/g and molecular weight of about 800,000 and BF-17, which is a borate (boron) free guar of charge density of about 1.7 meq/g and M. W.t of about 800,000 both available from ASI.

The hair care compositions may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β(1-4) glycosidic linkages. The galactose branching arises by way of an α(1-6) linkage. The ratio of mannose monomers to galactose monomers varies according to the species of the plant and also is affected by climate. Non Guar Galactomannan polymer derivatives can have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and Cassia gum (5 parts mannose/1 part galactose).

In one embodiment of the invention, the non-guar galactomannan polymer derivatives have a M. Wt. from about 1,000 to about 1,000,000, and/or form about 5,000 to about 900,000.

The hair care compositions of the can also include galactomannan polymer derivatives which have a cationic charge density from about 0.5 meq/g to about 7 meq/g. In one embodiment, the galactomannan polymer derivatives have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

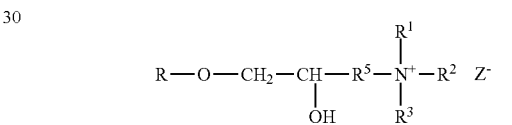

wherein R is the gum. The cationic galactomannan derivative can be a gum hydroxypropyltrimethylammonium chloride, which can be more specifically represented by the general formula 7:

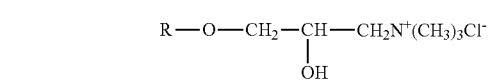

Alternatively the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a molecular weight of about 50,000 g/mol to about 1,000,000 g/mol, and/or from about 100,000 g/mol to about 900,000 g/mol and a cationic charge density from about 1 meq/g to about 5 meq/g, and/or from 2 meq/g to about 4 meq/g and can also be derived from a cassia plant.

The hair care compositions can comprise at least about 0.05% of a galactomannan polymer derivative by weight of the composition, alternatively from about 0.05% to about 2%, by weight of the composition, of a galactomannan polymer derivative.

The hair care compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The hair care compositions can comprise cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers for use in the hair care compositions can have a molecular weight about 50,000 g/mol to about 1,000,000 g/mol and/or from about 100,000 g/mol to about 1,000,000 g/mol.

The hair care compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in hair care compositions are available from known starch suppliers. Also suitable for use in hair care compositions are nonionic modified starch that can be further derivatized to a cationically modified starch as is known in the art. Other suitable modified starch starting materials may be quaternized, as is known in the art, to produce the cationically modified starch polymer suitable for use in hair care compositions.

Starch Degradation Procedure: a starch slurry can be prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

The hair care composition can comprise a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

The cationic copolymer can comprise:

(i) an acrylamide monomer of the following Formula AM:

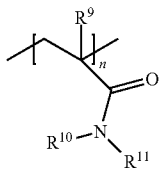

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

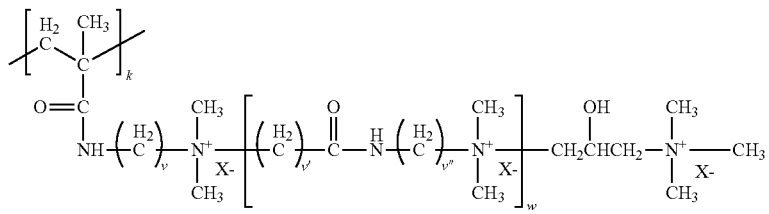

Formula CM where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

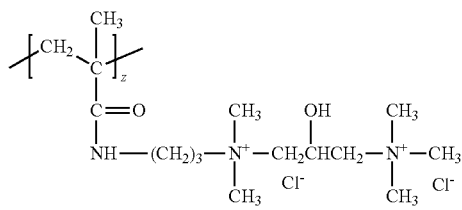

The above structure may be referred to as diquat. Alternatively, the cationic monomer can conform to Formula CM and wherein v and v" are each 3, v'=1, w=1, y=1 and $X^-$ is $Cl^-$, such as:

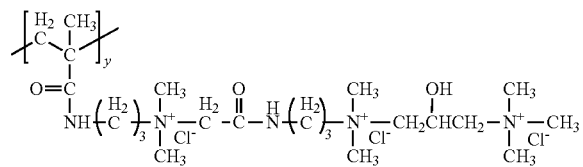

The above structure may be referred to as triquat.

Suitable acrylamide monomer include, but are not limited to, either acrylamide or methacrylamide.

In an alternative embodiment, the cationic copolymer is of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can comprise a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. In an embodiment, cationized esters of the (meth)acrylic acid containing a quaternized N atom are quaternized dialkylaminoalkyl (meth)acrylates with C1 to C3 in the alkyl and alkylene groups. Suitable cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. In an embodiment, the cationized esters of the (meth)acrylic acid containing a quaternized N atom is dimethylaminoethyl acrylate, which is quaternized with an alkyl halide, or with methyl chloride or benzyl chloride or dimethyl sulfate (ADAME-Quat). the cationic monomer when based on (meth)acrylamides can be quaternized dialkylaminoalkyl (meth)acrylamides with C1 to C3 in the alkyl and alkylene groups, or dimethylaminopropylacrylamide, which is quaternized with an alkyl halide, or methyl chloride or benzyl chloride or dimethyl sulfate.

Suitable cationic monomer based on a (meth)acrylamide include quaternized dialkylaminoalkyl(meth)acrylamide with C1 to C3 in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

The cationic copolymer can have a molecular weight from about 10 thousand g/mol to about 1 million g/mol, or from about 25 thousand g/mol to about 1 million g/mol, or from about 50 thousand g/mol to about 1 million g/mol, or from about 100 thousand g/mol to about 1.0 million g/mol, or from about 150 thousand g/mol to about 1.0 million g/mol.

The hair care composition can comprise a cationic synthetic polymer that may be formed from one or more cationic monomer units, and optionally one or more monomer units bearing a negative charge, and/or a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers having the following structure:

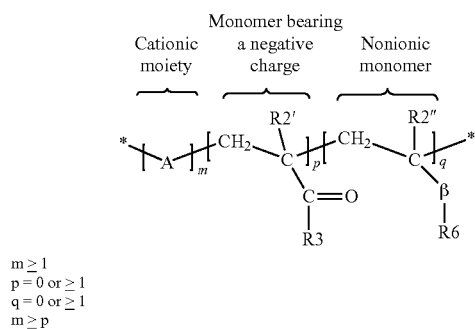

$m \geq 1$
$p = 0$ or $\geq 1$
$q = 0$ or $\geq 1$
$m \geq p$ where A, may be one or more of the following cationic moieties:

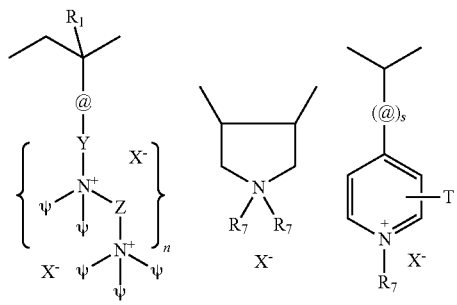

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl aryloxy;
where Z=C1-C22 alkyl, alkyloxy, aryl or aryloxy;
where R1=H, C1-C4 linear or branched alkyl;
where s=0 or 1, n=0 or ≥1;
where T and R7=C1-C22 alkyl; and
where X-=halogen, hydroxide, alkoxide, sulfate or alkylsulfate.

Where the monomer bearing a negative charge is defined by R2'=H, C1-C4 linear or branched alkyl and R3 as:

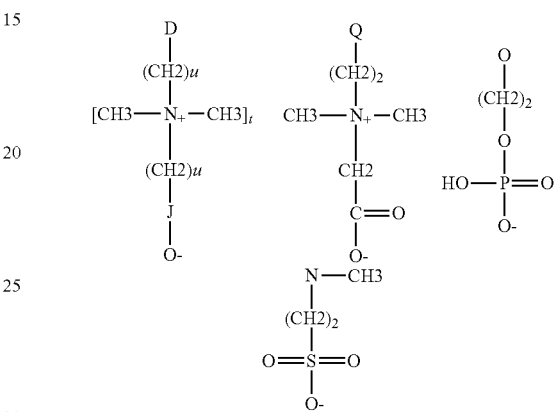

where D=O, N, or S;
where Q=NH$_2$ or O;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

and
where G' and G" are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X−) in association with the synthetic cationic polymers may be any known counterion so long as the polymers remain soluble or dispersible in water, in the hair care composition, or in a coacervate phase of the hair care composition, and so long as the counterions are physically and chemically compatible with the essential components of the hair care composition or do not otherwise unduly impair product performance, stability or aesthetics. Non limiting examples of such counterions include halides (e.g., chlorine, fluorine, bromine, iodine), sulfate and methylsulfate.

The concentration of the cationic polymers ranges about 0.025% to about 5%, from about 0.1% to about 3%, and/or from about 0.2% to about 1%, by weight of the hair care composition.

Suitable cationic cellulose polymers are salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Thickening Polymers

The hair care composition can comprise a thickening polymer to increase the viscosity of the composition. Suitable thickening polymers can be used. The hair care composition can comprise from about 0.1% to about 5% of a thickening polymer, from about 0.2% to about 2% of a thickening polymer. The thickening polymer modifier may be a polyacrylate, polyacrylamide thickeners. The thickening polymer may be an anionic thickening polymer.

The hair care composition may comprise thickening polymers that are homopolymers based on acrylic acid, methacrylic acid or other related derivatives, non-limiting examples include polyacrylate, polymethacrylate, polyethylacrylate, and polyacrylamide.

The thickening polymers may be alkali swellable and hydrophobically-modified alkali swellable acrylic copolymers or methacrylate copolymers, non-limiting examples include acrylic acid/acrylonitrogens copolymer, acrylates/steareth-20 itaconate copolymer, acrylates/ceteth-20 itaconate copolymer, Acrylates/Aminoacrylates/C10-30 Alkyl PEG-20 Itaconate Copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, Acrylates/Palmeth-25 Acrylate Copolymer, Acrylic Acid/Acrylamidomethyl Propane Sulfonic Acid Copolymer, and acrylates/C10-C30 alkyl acrylate crosspolymer.

The thickening polymers may be soluble crosslinked acrylic polymers, a non-limiting example includes carbomers.

The thickening polymers may be an associative polymeric thickeners, non-limiting examples include: hydrophobically modified, alkali swellable emulsions, non-limiting examples include hydrophobically modified polypolyacrylates; hydrophobically modified polyacrylic acids, and hydrophobically modified polyacrylamides; hydrophobically modified polyethers wherein these materials may have a hydrophobe that can be selected from cetyl, stearyl, oleayl, and combinations thereof.

The thickening polymers may be used in combination with polyvinylpyrrolidone, crosslinked polyvinylpyrrolidone and derivatives. The thickening polymers may be combined with polyvinyalcohol and derivatives. The thickening polymers may be combined with polyethyleneimine and derivatives.

The thickening polymers may be combined with alginic acid based materials, non-limiting examples include sodium alginate, and alginic acid propylene glycol esters.

The thickening polymers may be used in combination with polyurethane polymers, non-limiting examples include: hydrophobically modified alkoxylated urethane polymers, non-limiting examples include PEG-150/decyl alcohol/SMDI copolymer, PEG-150/stearyl alcohol/SMDI copolymer, polyurethane-39.

The thickening polymers may be combined with an associative polymeric thickeners, non-limiting examples include: hydrophobically modified cellulose derivatives; and a hydrophilic portion of repeating ethylene oxide groups with repeat units from 10-300, from 30-200, and from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

The thickening polymers may be combined with cellulose and derivatives, non-limiting examples include microcrystalline cellulose, carboxymethylcelluloses, hydroxyethylcellulose, hydroxypropylcellulose, hydroxypropyl methylcellulose, methylcellulose, ethyl cellulose; nitro cellulose; cellulose sulfate; cellulose powder; hydrophobically modified celluloses.

The thickening polymers may be combined with a guar and guar derivatives, non-limiting examples include hydroxypropyl guar, and hydroxypropyl guar hydroxypropyl trimonium chloride.

The thickening polymers may be combined with polyethylene oxide; polypropylene oxide; and POE-PPO copolymers.

The thickening polymers may be combined with polyalkylene glycols characterized by the general formula:

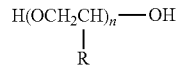

wherein R is hydrogen, methyl, or mixtures thereof, preferably hydrogen, and n is an integer having an average from 2,000-180,000, or from 7,000-90,000, or from 7,000-45,000. Non-limiting examples of this class include PEG-7M, PEG-14M, PEG-23M, PEG-25M, PEG-45M, PEG-90M, or PEG-100M.

The thickening polymers may be combined with silicas, non-limiting examples include fumed silica, precipitated silica, and silicone-surface treated silica.

The thickening polymers may be combined with water-swellable clays, non-limiting examples include laponite, bentolite, montmorilonite, smectite, and hectonite.

The thickening polymers may be combined with gums, non-limiting examples include xanthan gum, guar gum, hydroxypropyl guar gum, Arabia gum, tragacanth, galactan, carob gum, karaya gum, and locust bean gum.

The thickening polymers may be combined with, dibenzylidene sorbitol, karaggenan, pectin, agar, quince seed (Cydonia oblonga Mill), starch (from rice, corn, potato, wheat, etc), starch-derivatives (e.g. carboxymethyl starch, methylhydroxypropyl starch), algae extracts, dextran, succinoglucan, and pulleran, Non-limiting examples of thickening polymers include acrylamide/ammonium acrylate copolymer (and) polyisobutene (and) polysorbate 20; acrylamide/sodium acryloyldimethyl taurate copolymer/isohexadecane/polysorbate 80, ammonium acryloyldimethyltaurate/VP copolymer, Sodium Acrylate/Sodium Acryloyldimethyl Taurate Copolymer, acrylates copolymer, Acrylates Crosspolymer-4, Acrylates Crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil; carbomer, sodium carbomer, crosslinked polyvinylpyrrolidone (PVP), polyacrylamide/C13-14 isoparaffin/laureth-7, polyacrylate 13/polyisobutene/polysorbate 20, polyacrylate crosspolymer-6, polyamide-3, polyquaternium-37 (and) hydrogenated polydecene (and) trideceth-6, Acrylamide/Sodium Acryloyldimethyltaurate/Acrylic Acid Copolymer, sodium acrylate/acryloyldimethyltaurate/dimethylacrylamide, crosspolymer (and) isohexadecane (and) polysorbate 60, sodium polyacrylate. Exemplary commercially-available thickening polymers include ACULYN™ 28, ACULYN™ 88, ACULYN™ 33, ACULYN™ 22, ACULYN™ Excel, Carbopol® Aqua SF-1, Carbopol® ETD 2020, Carbopol® Ultrez 20, Carbopol® Ultrez 21, Carbopol® Ultrez 10, Carbopol® Ultrez 30, Carbopol® 1342, Carbopol® Aqua SF-2 polymer, Sepigel™ 305, Simulgel™ 600, Sepimax Zen, Carbopol® SMART 1000, Rheocare® TTA, Rheomer® SC-Plus, STRUCTURE® PLUS, Aristoflex® AVC, Stabylen 30, and combinations thereof.

Scalp Health Agents

In the present invention, one or more scalp health agent may be added to provide scalp benefits in addition to the anti-fungal/anti-dandruff efficacy provided by the surfactant soluble anti-dandruff agents. This group of materials is varied and provides a wide range of benefits including moisturization, barrier improvement, anti-fungal, anti-microbial and anti-oxidant, anti-itch, and sensates, and additional anti-dandruff agents such as polyvalent metal salts of pyrithione, non-limiting examples include zinc pyrithione (ZPT) and copper pyrithione, sulfur, or selenium sulfide. Such scalp health agents include but are not limited to: vitamin E and F, salicylic acid, niacinamide, caffeine, panthenol, zinc oxide, zinc carbonate, basic zinc carbonate, glycols, glycolic acid, PCA, PEGs, erythritol, glycerin, triclosan, lactates, hyaluronates, allantoin and other ureas, betaines, sorbitol, glutamates, xylitols, menthol, menthyl lactate, iso cyclomone, benzyl alcohol, a compound comprising the following structure:

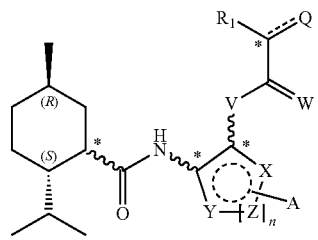

$R_1$ is selected from H, alkyl, amino alkyl, alkoxy;
$Q=H_2$, O, $-OR_1$, $-N(R_1)_2$, $-OPO(OR_1)_x$, $-PO(OR_1)_x$, $-P(OR_1)_x$ where x=1-2;

V=NR$_1$, O, —OPO(OR$_1$)$_x$, —PO(OR$_1$)$_x$, —P(OR$_1$)$_x$ where x=1-2;

W=H$_2$, O;

X, Y=independently selected from H, aryl, naphthyl for n=0;

X, Y=aliphatic CH$_2$ or aromatic CH for n≥1 and Z is selected from aliphatic CH$_2$, aromatic CH, or heteroatom;

A=lower alkoxy, lower alkylthio, aryl, substituted aryl or fused aryl; and stereochemistry is variable at the positions marked*.

and natural extracts/oils including peppermint, spearmint, argan, jojoba and aloe.

Blowing Agent

The hair care composition described herein may comprise from about from about 1% to about 15% blowing agent, from about 3% to about 10%, and alternatively from about 4% to about 7% blowing agent, by weight of the hair care composition.

The blowing agent may comprise one or more volatile materials, which in a gaseous state, may carry the other components of the hair care composition in particulate or droplet form. The blowing agent may have a boiling point within the range of from about −45° C. to about 5° C. The blowing agent may be liquefied when packaged in convention aerosol containers under pressure. The rapid boiling of the blowing agent upon leaving the aerosol foam dispenser may aid in the atomization of the other components of the hair care composition.

Aerosol blowing agents which may be employed in the aerosol composition may include the chemically-inert hydrocarbons such as propane, n-butane, isobutane, cyclopropane, and mixtures thereof, CO$_2$/carbon dioxide, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and mixtures thereof. Non-limiting examples of a blowing agent may be Propellant A46 (Isobutane and Propane) (18, Diversified Cpc International (Channahon US) and HFO (Trans 1,3,3,3 Tetrafluroprop 1 ene) (19) from Honey Well. The blowing agent may comprise hydrocarbons such as isobutane, propane, and butane—these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar.

Optional Ingredients

The hair care composition may further comprise one or more optional ingredients, including benefit agents Suitable benefit agents include, but are not limited to conditioning agents, cationic polymers silicone emulsions, anti-dandruff actives, gel networks, chelating agents, and, natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

Conditioning Agents

The conditioning agent of the hair care compositions can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference.

The silicone conditioning agents suitable for use can have a viscosity, as measured at 25° C., from about 20 to about 2,000,000 centistokes ("csk"), of from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 10 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant, Other classes of silicones suitable for use include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

The conditioning agent of the hair care compositions may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Emulsifiers

A variety of anionic and nonionic emulsifiers can be used in the hair care composition. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

Aqueous Carrier

The hair care compositions can be in the form of pourable liquids (under ambient conditions). Such compositions will therefore typically comprise a carrier, which is present at a level of from about 40% to about 80%, alternatively from about 45% to about 75%, alternatively from about 50% to about 70% by weight of the hair care composition. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in the hair care compositions includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Foam Dispenser

The hair care composition described herein may be provided in a foam dispenser. The foam dispenser may be an aerosol foam dispenser, a bag-on-valve type, dip tube type, piston type, or other conventional types. The aerosol foam dispenser may comprise a reservoir for holding the hair treatment composition. The reservoir may be made out of any suitable material selected from the group consisting of plastic, metal, alloy, laminate, and combinations thereof. The reservoir may be for one-time use. The reservoir may be removable from the aerosol foam dispenser. Alternatively, the reservoir may be integrated with the aerosol foam dispenser. And there may be two or more reservoirs.

Test Methods

In Vivo Scalp Depo

The on-scalp deposition of the anti-dandruff active is measured by having the hair of individuals washed with a composition comprising an anti-dandruff active, for example a composition pursuant to the present invention. A trained cosmetician will dose the liquid shampoo control at 5 g on ½ of the panelist scalp and wash according to conventional washing protocol. Then 2.5 g of foam is dosed to the other half of the panelist head and washed according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

Sebum Clean Method

Clean hair switches are obtained for testing. Artificial sebum is warmed and mixed with Uvitex OB. The oil and Uvitex OB mixture is applied to a 3.5 inch area designated along the body of the hair switch. Consistent oil treatment occurs upon each switch treated. Dosage of shampoo to hair is approximately 0.1 cc per gram of hair. Hair switches are wet for 15 seconds. Product is applied from top to bottom of the hair. Shampoo is milked into the hair hand over hand for approximately 30 seconds. The switches are rinsed and squeezed to remove excess water. Switches are then dried in a heat box. Oil absorbent sheets are applied with one hand and wrapped around the back of the hair switch. Moderate pressure is applied while pulling the oil absorbent sheet down the hair tress. Oil absorbent sheets are exposed to a black light and rated based on their level of glow where 0=no glow and 5=full glow.

Wet Feel Sensory

The wet feel sensory test is performed via trained panelists. Hair switches are prewet and squeegeed to remove excess water. Product application occurs to the front and back of a hair switch at a given relevant weight of shampoo per weight of hair switch. Foam products are dosed at ½ the dose vs. full dose liquid control Example 17. Example 13 Foam is ½ dosed vs. Example 13 as a liquid ½ dose is performed to evaluate the effect of foam form vs. liquid form from within the same formula. Product is spread in a controlled manner to saturate the hair switch. The wet feel attributes are addressed in the following order according to established sensory protocols for Rinse Count Drag, Coated Feel, Slippery Feel and Force to Comb. A rating scale of 0-14 is used for each evaluating.

Dry Feel Sensory

The Dry feel sensory test performed via trained panelists. Panelist clean fingers with alcohol prior to and in between each tactile evaluation. Hair switches go through the wet sensory treatment protocol for application prior to evaluation. Hair is dried in a hot box. Panelist evaluate Smoothness, force to comb the body of the hair and force to comb the ends. Smoothness is ranked from least smooth to most smooth. The force to comb body and ends are evaluated from least force to comb to most force to comb.
The percent agent deposited can be calculated using the following equation:

$$\% \text{ agent deposited} = \frac{\frac{\text{grams of agent deposited}}{\text{area of scalp extracted}}}{\frac{(\text{wt. \% agent in shampoo}) \times (\text{grams of shampoo applied})}{\text{area of scalp treated}}} \times 100$$

Sample Calculation for % Piroctone Olamine deposited, where:
Grams of agent deposited=$1.7 \times 10^{-6}$ g
Area of scalp extracted=1 cm$^2$
Wt % Piroctone Olamine in shampoo=1.0%
Grams of shampoo applied=5 g
Area of scalp treated=300 cm$^2$ $$\% \text{ Piroctone Olamine deposited} = \frac{\frac{1.7 \times 10^{-6} \text{ g}}{1 \text{ cm}^2}}{\frac{(1.0\%) \times (5 \text{ g})}{300 \text{ cm}^2}} \times 100\%$$

% Piroctone Olamine deposited = 1.02%

The deposition efficiency can be calculated using the following equation:

$$\text{Deposition efficiency} = \frac{\% \text{ agent deposited by example formula}}{\% \text{ agent deposited by control formula}}$$

Sample calculation for deposition efficiency, where:
% Piroctone Olamine deposited by example formula=1.92%
% Piroctone Olamine deposited by control formula=1.02%

$$\text{Deposition efficiency} = \frac{1.92\%}{1.02\%}$$

Deposition efficiency = 1.9X

Depo Results

Examples (1,2) high surfactant formulations (24% total surfactant) show that when foams are dosed at ½ the wt. vs. control liquid, to account for equal % Piroctone Olamine delivered vs. liquid control Example 15, depo efficiency of 1.4× more than liquid method control Example 15. Sample 3 shows that when formula concentration is lowered from 1% to 0.8% PO but dose is adjusted to deliver equal PO concentration to the scalp as liquid method control at 0.5% on scalp, depo efficiency still remains more efficient at 1.2× more than method control Example 15. The lowering of total surfactant to 23%, as observed in Examples (4,5,6) results in 1.7× more efficient depo vs liquid method control Example 15.

When surfactant level is decreased to (12.5-9%), as observed in examples 7-14,18 one can see that depo efficiency trend ranges from 1.9×-2.7× over liquid control Example 15. It is believed that this result for low surfactant formulations is due to PO active being close to the solubility limit within the given surfactant system. The closer that one can be to the solubility limit the potential higher ability to deliver the Piroctone Olamine from the formulation upon dilution. Therefore, the choice of surfactant systems is very important in delivering Piroctone Olamine. Additionally, the choice of propellant type can also aid or inhibit the ability of PO to deposit. The type and concentration of propellant may swell the micelle, elongate the micelle, or not enter the micelle depending on how hydrophilic or hydrophobic the propellant may be. Therefore, choice of propellants is also very important when trying to deliver soluble drug active to the scalp effectively.

In the present invention the foaming composition may have a deposition efficiency of >1.7× that of a control composition that deposits about 1% of a mass of surfactant soluble antidandruff active dosed.

Sequential Monadic Team Test (n=9)
Methodology

Low surfactant and high surfactant Foam shampoos are placed among panelist. Panelists receive one bottle of Foam shampoo labeled for the consumer test, printed instructions with visuals and printed survey. They are asked to use the 1$^{st}$ Foam shampoo product for at least 3 consecutive times before answering questions on the provided survey. Then, they are asked to return the 1$^{st}$ product to avoid any confusion during the usage period of the 2$^{nd}$ product. The 2$^{nd}$ product is instructed to be used in the same way as the 1$^{st}$ product before responding the provided survey.

| SEQUENTIAL MONADIC TEAM TEST Number of People (n = 9) (BASED ON 0-100 SCALE) | | | |
| --- | --- | --- | --- |
| # PEOPLE WHO RATED | Leaving hair and scalp FEELING CLEAN when wet | Ability to clean SCALP | Ability to clean HAIR |
| EXAMPLE 9 (LOW SURFACTANT) BETTER THAN EXAMPLE 3 (HIGH SURFACTAT) | 4 | 3 | 2 |
| EXAMPLE 9 (LOW SURFACTANT) = EXAMPLE 3 (HIGH SURFACTANT) | 4 | 4 | 5 |
| EXAMPLE 3 (HIGH SURFACTANT) BETTER THAN EXAMPLE 9 (LOW SURFACTANT) | 1 | 2 | 2 |

Results

The data indicates that more responders rated that the low surfactant (Example 9) foam is equal to or better than the high surfactant (Example 3) for the attributes of "leaving Hair and scalp feeling clean when wet, Ability to clean scalp, and ability to clean hair."

Hair Sensory Data for Wet and Dry Feel Conditioning Key
(1 Most Conditioned to 3 Least Conditioned)

|  | Liquid Shampoo control Exmaple 17 (Full Dosed) | Example 13 (Foam ½ Dosed) | Example 13 Liquid version (½ Dosed) | Example 9 (Foam ½ Dosed) |
|---|---|---|---|---|
| Wet Feel Sensory |  |  |  |  |
| Rinse Count Drag (Clean feel) | 3 | 1 | 2 | NA |
| Coated | 3 | 1 | 2 | NA |
| Slip | 3 | 1 | 2 | NA |
| Force to comb | 3 | 1 | 2 | NA |
| Smoothness | 3 | 1 | 2 | NA |
| Resistance | 3 | 1 | 2 | NA |
| Dry Feel Sensory |  |  |  |  |
| Smoothness | 3 | 1 | NA | 2 |
| Force to Comb (Body) | 3 | 1 | NA | 2 |
| Force to Comb (Ends) | 3 | 1 | NA | 2 |

Least conditioned  More conditioned  Most conditioned
3                  2                 1

Results:

Data indicates that the foam Example 13 at ½ dose is the most conditioned when compared to a high conditioning liquid market control shampoo example 17 at full dose. Example 13 liquid version (no propellant added) and dosed at ½ dose to single variably test the foam form vs. a the liquid form at the same weighted dose. It is observed that the liquid version of example 13 does not condition as well for wet feel via the sensory response. Example 9 formula is another example that shows that increasing surfactant from Example 13 at 9% total surfactant to 12.5% still maintains a more dry conditioning vs. the market liquid control Example 17. Example 13 foam maintains most dry conditioning over Example 17 and Example 9.

Method of Making

The following examples illustrate non-limiting examples of the invention described herein. The exemplified hair care compositions may be made by mixing together water, polymer, and surfactants along with Sodium Xylene Sulfonate or rheology modifier to thin surfactant phase. The ingredients are mixed thoroughly at ambient temperature. Additional ingredients, including blowing agent, electrolytes, silicone emulsions, preservatives and fragrances may be added to the product. It will be appreciated that other modifications of the hair care compositions within the skill of those in the formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following examples illustrate non-limiting examples of the invention described herein. All parts, percentages, and ratios herein are by weight unless otherwise specified. Some components may come from suppliers as dilute solutions. The amount stated reflects the weight percent of the active material, unless otherwise specified. The below table are non-limiting examples of hair care compositions described herein:

TABLE 1

| Ingredients | Ex. 1 | Ex. 2 | Ex. 3 | Ex. 4 | Ex. 5 |
|---|---|---|---|---|---|
| Form | Foam | Foam | Foam | Foam | Foam |
| (1) Sodium Laureth Sulfate (SLE1S) | 18 | 18 | 18 | 18 | 18 |
| (2) Sodium Laureth Sulfate (SLE3S) | 0 | 0 | 0 | 0 | 0 |
| (3) Sodium Lauryl sulfate | 0 | 0 | 0 | 0 | 0 |
| (4) Sodium Trideceth 2 sulfate | 6 | 6 | 6 | 5 | 5 |
| (5) Cocamidopropyl Betaine | 0 | 0 | 0 | 0 | 0 |
| (6) Cocamide MEA | 0 | 0 | 0 | 0 | 0 |
| (7) Dehyrdorxyxanthan gum | 0 | 0 | 0 | 0 | 0 |
| (8) Glycol Distearate | 0 | 0 | 0 | 0 | 0 |
| (9) Glycerin | 0 | 0 | 0 | 0 | 0 |
| (10) Piroctone Olamine | 1 | 1 | 0.8 | 0.8 | 0.8 |
| (11) Zinc Pyrithione | 0 | 0 | 0 | 0 | 0 |
| (12) Zinc Carbonate | 0 | 0 | 0 | 0 | 0 |
| (13) Fragrance | 2 | 1.5 | 2 | 1.5 | 1.5 |
| (14) BF 17 HMW Guar | 0 | 0 | 0 | 0 | 0 |
| (15) Guar Hydroxypropyltrimonium Chloride (N-Hance 3196) | 0.4 | 0.4 | 0.4 | 0.4 | 0.4 |
| (16) Guar Hyrdoxypropyltrimonium Chloride (LMW) | 0 | 0 | 0 | 0 | 0.4 |
| (17) Polyquaternium 10 | 0 | 0 | 0 | 0 | 0.4 |
| (18) PEG23M | 0.1 | 0.1 | 0.1 | 0 | 0 |
| (19) Dimethicone DM5500 | 0 | 0 | 0 | 0 | 0 |

TABLE 1-continued

| Ingredient | | | | | |
|---|---|---|---|---|---|
| (20) Hydrochloric acid | 0 | 0 | 0 | 0 | 0 |
| (21) Preservative | 0.033 | 0.033 | 0.033 | 0.033 | 0.033 |
| (22) Sodium Xylene Sulfonate (QS to viscosity target) | QS | QS | QS | QS | QS |
| (23) Citric Acid | 0.6 | 0.6 | 0.6 | 0.6 | 0.6 |
| (24) Sodium Benzoate | 0.15 | 0.15 | 0.15 | 0.15 | 0.15 |
| (25) Dimethicone DC330M | 0 | 0 | 0 | 0 | 0 |
| (26) Tetrasodium EDTA Tetrahydrate | 0.15 | 0.15 | 0.15 | 0.15 | 0.15 |
| (27) Water and Minors (QS to 100%) | QS | QS | QS | QS | QS |
| (28) Blowing Agent A46 (Isobutane and Propane) | 5 | 0 | 5 | 5 | 5 |
| (29) Blowing Agent HF0 (trans-1,3,3,3-tetrafluroprop-1-ene) | 0 | 5 | 0 | 0 | 0 |
| pH | 6.5 | 6.5 | 6.5 | 4.5 | 4.5 |
| Total surfactant (active) | 24 | 24 | 24 | 23 | 23 |
| Invivo Scalp Depo of Piroctone Olamine | | | | | |
| Product Dosed wt (g) | 2.5 | 2.5 | 3.5 | 2.5 | 2.5 |
| Average Depo □g/cm2 | 1.3 | 1.3 | 1.2 | 1.2 | 1.2 |
| % Depo | 1.6% | 1.6% | 1.3% | 1.8% | 1.8% |
| Efficiency vs. method control Example 15 | 1.4 | 1.4 | 1.2 | 1.7 | 1.7 |
| Hair Switch Sebum Cleaning method | | | | | |
| Sebum cleaning scale (0-5 rating) No oil control switch (0 rating), Oil treated switch (5 rating) | | 1 | | | |

| Ingredients | Ex. 6 | Ex. 7 | Ex. 8 | Ex. 9 | Ex. 10 |
|---|---|---|---|---|---|
| Form | Foam | Foam | Foam | Foam | Foam |
| (1) Sodium Laureth Sulfate (SLE1S) | 18 | 9 | 9 | 12.5 | 12.5 |
| (2) Sodium Laureth Sulfate (SLE3S) | 0 | 0 | 0 | 0 | 0 |
| (3) Sodium Lauryl sulfate | 0 | 0 | 0 | 0 | 0 |
| (4) Sodium Trideceth 2 sulfate | 5 | 3 | 3 | 0 | 0 |
| (5) Cocamidopropyl Betaine | 0 | 0 | 0 | 0 | 0 |
| (6) Cocamide MEA | 0 | 0 | 0 | 0 | 0 |
| (7) Dehyrdorxyxanthan gum | 0 | 0 | 0 | 0.25 | 0.25 |
| (8) Glycol Distearate | 0 | 1.5 | 1.5 | 1.5 | 1.5 |
| (9) Glycerin | 0 | 0 | 0 | 0 | 0 |
| (10) Piroctone Olamine | 0.8 | 1 | 1 | 0.8 | 1 |
| (11) Zinc Pyrithione | 0 | 0 | 0 | 0 | 0 |
| (12) Zinc Carbonate | 0 | 0 | 0 | 0 | 0 |
| (13) Fragrance | 1.5 | 1.5 | 1.5 | 1.5 | 1.5 |
| (14) BF 17 HMW Guar | 0 | 0 | 0 | 0 | 0 |
| (15) Guar Hydroxypropyltrimonium Chloride (N-Hance 3196) | 0.8 | 0.4 | 0.4 | 0 | 0 |
| (16) Guar Hyrdroxypropyltrimonium Chloride (LMW) | 0 | 0 | 0 | 0 | 0 |
| (17) Polyquaternium 10 | 0 | 0 | 0 | 0 | 0 |
| (18) PEG23M | 0 | 0.1 | 0.1 | 0 | 0 |
| (19) Dimethicone DM5500 | 0 | 0 | 0 | 0 | 0 |
| (20) Hydrochloric acid | 0 | 0 | 0 | 0 | 0 |
| (21) Preservative | 0.033 | 0.033 | 0.033 | 0.033 | 0.033 |
| (22) Sodium Xylene Sulfonate (QS to viscosity target) | QS | QS | QS | QS | QS |
| (23) Citric Acid | 0.6 | 0.6 | 0.6 | 0.6 | 0.6 |
| (24) Sodium Benzoate | 0.15 | 0.15 | 0.15 | 0.15 | 0.15 |
| (25) Dimethicone DC330M | 0 | 0 | 0 | 4 | 4 |
| (26) Tetrasodium EDTA Tetrahydrate | 0.15 | 0.15 | 0.15 | 0.15 | 0.15 |
| (27) Water and Minors (QS to 100%) | QS | QS | QS | QS | QS |
| (28) Blowing Agent A46 (Isobutane and Propane) | 5 | 5 | 0 | 5 | 5 |
| (29) Blowing Agent HF0 (trans-1,3,3,3-tetrafluroprop-1-ene) | 0 | 0 | 5 | 0 | 0 |
| pH | 4.5 | 6.5 | 6.5 | 4.5 | 4.5 |
| Total surfactant (active) | 23 | 12 | 12 | 12.5 | 12.5 |
| Invivo Scalp Depo of Piroctone Olamine | | | | | |
| Product Dosed wt (g) | 2.5 | 2.5 | 2.5 | 2.5 | 2.5 |
| Average Depo □g/cm2 | 1.2 | 2 | 2 | 1.4 | 2 |
| % Depo | 1.8% | 2.4% | 2.4% | 2.1% | 2.4% |
| Efficiency vs. method control Example 15 | 1.7 | 2.2 | 2.2 | 1.9 | 2.2 |
| Hair Switch Sebum Cleaning method | | | | | |
| Sebum cleaning scale (0-5 rating) No oil control switch (0 rating), Oil treated switch (5 rating) | | 2 | | | 1 |

TABLE 1-continued

| Ingredients | Ex. 11 | Ex. 12 | Ex. 13 | Ex. 14 |
|---|---|---|---|---|
| Form | Foam | Foam | Foam | Foam |
| (1) Sodium Laureth Sulfate (SLE1S) | 9 | 9 | 9 | 9 |
| (2) Sodium Laureth Sulfate (SLE3S) | 0 | 0 | 0 | 0 |
| (3) Sodium Lauryl sulfate | 0 | 0 | 0 | 0 |
| (4) Sodium Trideceth 2 sulfate | 0 | 0 | 0 | 0 |
| (5) Cocamidopropyl Betaine | 0 | 0 | 0 | 0 |
| (6) Cocamide MEA | 0 | 0 | 0 | 0 |
| (7) Dehyrdorxyxanthan gum | 0.25 | 0.25 | 0.25 | 0 |
| (8) Glycol Distearate | 1.5 | 1.5 | 1.5 | 1.5 |
| (9) Glycerin | 0 | 0 | 0 | 0 |
| (10) Piroctone Olamine | 1 | 1 | 1 | 1 |
| (11) Zinc Pyrithione | 0 | 0 | 0 | 0 |
| (12) Zinc Carbonate | 0 | 0 | 0 | 0 |
| (13) Fragrance | 1.5 | 1.5 | 1.5 | 1.5 |
| (14) BF 17 HMW Guar | 0 | 0.25 | 0 | 0 |
| (15) Guar Hydroxypropyltrimonium Chloride (N-Hance 3196) | 0 | 0 | 0 | 0 |
| (16) Guar Hyrdroxypropyltrimonium Chloride (LMW) | 0 | 0 | 0 | 0 |
| (17) Polyquaternium 10 | 0 | 0 | 0 | 0 |
| (18) PEG23M | 0 | 0 | 0 | 0 |
| (19) Dimethicone DM5500 | 0 | 0 | 0 | 0 |
| (20) Hydrochloric acid | 0 | 0 | 0 | 0 |
| (21) Preservative | 0.033 | 0.033 | 0.033 | 0.033 |
| (22) Sodium Xylene Sulfonate (QS to viscosity target) | QS | QS | QS | QS |
| (23) Citric Acid | 0.6 | 0.6 | 0.6 | 0.6 |
| (24) Sodium Benzoate | 0.15 | 0.15 | 0.15 | 0.15 |
| (25) Dimethicone DC330M | 0 | 0 | 4 | 0 |
| (26) Tetrasodium EDTA Tetrahydrate | 0.15 | 0.15 | 0.15 | 0.15 |
| (27) Water and Minors (QS to 100%) | QS | QS | QS | QS |
| (28) Blowing Agent A46 (Isobutane and Propane) | 5 | 5 | 5 | 5 |
| (29) Blowing Agent HF0 (trans-1,3,3,3-tetrafluroprop-1-ene) | 0 | 0 | 0 | 0 |
| pH | 4 | 4 | 4 | 4 |
| Total surfactant (active) | 9 | 9 | 9 | 9 |
| Invivo Scalp Depo of Piroctone Olamine | | | | |
| Product Dosed wt (g) | 2.5 | 2.5 | 2.5 | 2.5 |
| Average Depo □g/cm2 | 2.4 | 2.4 | 2.4 | 2.4 |
| % Depo | 2.9% | 2.9% | 2.9% | 2.9% |
| Efficiency vs. method control Example 15 | 2.7 | 2.7 | 2.7 | 2.7 |

| Ingredients | Ex. 15 (Comparative) | Ex. 16 (Comparative) | Ex. 17 (Comparative) | Ex. 18 | Ex. 19 |
|---|---|---|---|---|---|
| Form | Liquid | Liquid | Liquid | Foam | Foam |
| (1) Sodium Laureth Sulfate (SLE1S) | 0 | 0 | 12.5 | 12.5 | 12.5 |
| (2) Sodium Laureth Sulfate (SLE3S) | 8 | 8 | 0 | 0 | 0 |
| (3) Sodium Lauryl sulfate | 7 | 7 | 0 | 0 | 0 |
| (4) Sodium Trideceth 2 sulfate | 0 | 0 | 0 | 0 | 0 |
| (5) Cocamidopropyl Betaine | 2 | 2 | 1.5 | 0 | 0 |
| (6) Cocamide MEA | 0 | 0 | 1.5 | 0 | 0 |
| (7) Dehyrdorxyxanthan gum | 0 | 0 | 0 | 0.25 | 0.25 |
| (8) Glycol Distearate | 1.5 | 1.5 | 1.5 | 1.5 | 1.5 |
| (9) Glycerin | 0 | 0 | 0 | 0 | 0 |
| (10) Piroctone Olamine | 0.5 | 1 | 0 | 0.8 | 0.8 |
| (11) Zinc Pyrithione | 0 | 0 | 1 | 0 | 0 |
| (12) Zinc Carbonate | 0 | 0 | 1.61 | 0 | 0 |
| (13) Fragrance | 0.85 | 0.85 | 0.85 | 1.5 | 1.5 |
| (14) BF 17 HMW Guar | 0 | 0 | 0 | 0 | 0 |
| (15) Guar Hydroxypropyltrimonium Chloride (N-Hance 3196) | 0.25 | 0.25 | 0 | 0 | 0 |
| (16) Guar Hyrdroxypropyltrimonium Chloride (LMW) | 0 | 0 | 0.3 | 0 | 0 |
| (17) Polyquaternium 10 | 0 | 0 | 0.2 | 0 | 0 |
| (18) PEG23M | 0 | 0 | 0 | 0.1 | 0.1 |
| (19) Dimethicone DM5500 | 0.8 | 0.8 | 0 | 0 | 0 |
| (20) Hydrochloric acid | 0 | 0 | QS | 0 | 0 |
| (21) Preservative | 0.033 | 0.033 | 0.033 | 0.033 | 0.033 |
| (22) Sodium Xylene Sulfonate (QS to viscosity target) | QS | QS | QS | QS | QS |
| (23) Citric Acid | 0.6 | 0.6 | 0 | 0.6 | 0.6 |
| (24) Sodium Benzoate | 0.15 | 0.15 | 0.15 | 0.15 | 0.15 |

TABLE 1-continued

| | | | | | |
|---|---|---|---|---|---|
| (25) Dimethicone DC330M | 0 | 0 | 2.7 | 0 | 4 |
| (26) Tetrasodium EDTA Tetrahydrate | 0.15 | 0.15 | 0 | 0.15 | 0.15 |
| (27) Water and Minors (QS to 100%) | QS | QS | QS | QS | QS |
| (28) Blowing Agent A46 (Isobutane and Propane) | 0 | 0 | 0 | 5 | 5 |
| (29) Blowing Agent HF0 (trans-1,3,3,3-tetrafluroprop-1-ene) | 0 | 0 | 0 | 0 | 0 |
| pH | 6 | 6 | 7 | 4.5 | 4.5 |
| Total surfactant (active) | 17 | 17 | 15.5 | 12.5 | 12.5 |
| Invivo Scalp Depo of Piroctone Olamine | | | | | |
| Product Dosed wt (g) | 5 | 5 | 2.5 | | |
| Average Depo □g/cm2 | 0.9 | 1.8 | 1.4 | | |
| % Depo | 1.1% | 1.1% | 2.1% | | |
| Efficiency vs. method control Example 15 | 1.0 | 1.0 | 1.9 | | |

(1). Sodium Laureth-1 Sulfate from the Stepan Company
(2). Sodium Laureth-3 Sulfate from the Stapan Company
(3). Sodium Lauryl Sulfate from the Stepan Company
(4). Sodium Tridecyl Ether Sulfate - 2 mol from Solvay (Blue Island US)
(5). Cocamidopropyl betaine High pH from Stepan Co Millsdale (Elwood US)
(6). Cocamide monoethanolamine, CMEA from Stepan Company
(7). Dehyrdorxyxanthan gum Amaze XT (Akzo Nobel)
(8). Glycol Distearate from Golschmidt Chemical Company
(9). Glycerin from P&G Chemicals
(10). Piroctone Olamine (Octopirox from Clariant)
(11). Zinc Pyrithione, U2 ZPT from Lonza
(12). Zinc Carbonate from Bruggeman Group
(13). Fragrance from P&G supplied
(14). Guar Hydroxypropyltrimonium Chloride, BF 17 HMW Guar from Ashland
(15). Guar Hydroxypropyltrimonium Chloride, NHance ™ 3196 from Ashland with a MW of 1,700,000 g/mol and charge density of 0.7 meq/g
(16). Guar Hydroxypropyltrimonium Chloride, Jaguar C500 from Solvay with a M. Wt of 500,000 g/mol and charge density of 0.8 meq/g
(17). Polyquaternium 10 from Dow Chemical
(18). Polyethylene Glycol, PEG 23M Polyox WSR N-1 2K from Amerchol Corp., Piscataway, NJ
(19). Dimethicone DM5500, Wacker Silicone
(20). Hydrochloric acid from Mallinckrodt Baker Inc.
(21). Preservative Kathon CG from Akzo Nobel
(22). Sodium Xylene Sulfonate from Stepan Company
(23). Citric Acid from Cargill Inc.
(24). Sodium Benzoate from Kalama Chemical
(25). Dimethicone DC330M Momentive
(26). Tetrasodium EDTA Tetrahydrate
(27). Water from Misty Mountain Spring Water
(28). Blowing Agent A46 (Isobutane and Propane) Diversified Cpc International (Channahon US)
(29). Blowing Agent HF0 (Trans 1,3,3,3 Tetrafluroprop-1-ene) from Honey Well Foam Rheology Method (Yield Point)

Foam shampoo is applied to the AR1000 rheometer for foam oscillation stress sweep. 60 mm smooth acrylic plate is utilized for shear stress measurement. Measurement is made at 25 C. The plate head is lowered to 1200 microns and excess foam is removed with a spatula so that drag does not occur during measurement. The measurement gap height is then lowered 1000 microns. Sweep occurs from 0.1 to 400 Pa. Data is analyzed via TA Rheology Advantage Data Analysis software. Yield point is determined at the point at which the oscillatory shear stress begins to deviate from its tangent. The yield point measurements are reported in Pa units.

The dosage of foam can have a yield point of from about 10 Pa to about 50 Pa, alternatively about 15 Pa to about 30 Pa, alternatively from about 20 Pa to about 30 Pa.

The dosage of foam can also have a foam density of from about 0.01 g/cm$^3$ to about 0.02 g/cm$^3$; alternatively from about 0.05 g/cm$^3$ to about 0.1 g/cm$^3$; and alternatively from about 0.07 g/cm$^3$ to about 0.1 g/cm$^3$.

Kruss Lather Analyzer (Bubble Size)

The commercially available Kruss lather analyzer DFA100, supplied from Kruss, is used to analyze the foam shampoo for the initial Sauter mean radius $R_{32}$ (bubble size). Shampoo foam is dispensed into the CY4571 column containing a prism. An internal stopper is placed into the column approximately 100 ml from the top of the chamber. The camera height is set to 244 mm and camera position is placed in the 3 slot. Structure foaming is captured at 2 frames per second for 120 seconds. Data analysis is performed on the Kruss Advance 1.5.1.0 software application version.

The dosage of foam can also have a bubble size distribution comprising an $R_{32}$ of from about 5 μm to about 100 μm, alternatively from about 5 μm to 90 μm, alternatively from about 10 μm to about 60 μm, alternatively from about 15 μm to about 50 μm, and alternatively from about 25 μm to about 40 μm.

| | Bubble size (R32 initial um) | Yield point (Pa) |
|---|---|---|
| Example 3 | 33 | 36 |
| Example 9 | 30 | 19 |
| Example 18 | 29 | 25 |
| Example 19 | 30 | 27 |

Results

All results Example 3, 9, 18, and 19 show similar bubble size measurements within the range of (29-33 um for R32 initial) indicating the high surfactant and low surfactant foams have similar foam structure. Yield point for Example 3 high surfactant foam results in a yield point of 36 (Pa). Low surfactant formula Example 9, 18, and 19 all show lower rheology (19, 25, 27 Pa respectively) indicating low surfactant is easier to spread or shear vs. the more viscoelastic Example 3.

TABLE 2

| Ingredients | Ex. 20 | Ex. 21 | Ex. 22 | Ex. 23 | Ex. 24 | Ex. 25 |
|---|---|---|---|---|---|---|
| Form | Foam | Foam | Foam | Foam | Foam | Foam |
| (1) Sodium Deceyl Sulfate | 0 | 0 | 0 | 0 | 13 | 0 |
| (2) Sodium Deceth sulfate | 0 | 0 | 0 | 0 | 0 | 7 |
| (3) Sodium Laureth Sulfate (SLE1S) | 0 | 0 | 0 | 6 | 0 | 6 |
| (4) Sodium Laureth Sulfate (SLE3S) | 9 | 13 | 0 | 6 | 0 | 0 |
| (5) Sodium Lauryl sulfate | 0 | 0 | 13 | 0 | 0 | 0 |
| (6) Sodium Trideceth 2 sulfate | 0 | 0 | 0 | 0 | 0 | 0 |
| (7) Cocamidopropyl Betaine | 0 | 0 | 0 | 0 | 0 | 0 |
| (8) Cocamide MEA | 0 | 0 | 0 | 0 | 0 | 0 |
| (9) Sodium Laureth Sulfosuccinate | 0 | 0 | 0 | 0 | 0 | 0 |
| (10) Sodium Cocoyl Alaninate | 0 | 0 | 0 | 0 | 0 | 0 |
| (11) Sodium Lauroyl Sarcosinate | 0 | 0 | 0 | 0 | 0 | 0 |
| (12) Dehyrdroxyxanthan gum | 0.25 | 0.25 | 0 | 0.25 | 0.25 | 0.25 |
| (13) Glycol Distearate | 1.5 | 1.5 | 0 | 0 | 1.5 | 0 |
| (14) Glycerin | 0 | 0 | 0 | 0 | 0 | 0 |
| (15) Piroctone Olamine | 0.8 | 0.8 | 0.8 | 1 | 0.8 | 1 |
| (16) Zinc Pyrithione | 0 | 0 | 0 | 0 | 0 | 0 |
| (17) Zinc Carbonate | 0 | 0 | 0 | 0 | 0 | 0 |
| (18) Fragrance | 1.5 | 1.5 | 1.5 | 1.5 | 1.5 | 1.5 |
| (19) BF 17 HMW Guar | 0 | 0 | 0.4 | 0 | 0 | 0 |
| (20) Guar Hydroxypropyltrimonium Chloride (N-Hance 3196) | 0 | 0 | 0 | 0 | 0 | 0 |
| (21) Guar Hyrdroxypropyltrimonium Chloride (LMW) | 0 | 0 | 0 | 0 | 0 | 0 |
| (22) Polyquaternium 10 | 0 | 0 | 0 | 0 | 0 | 0 |
| (23) PEG23M | 0 | 0 | 0 | 0 | 0 | 0 |
| (24) Dimethicone DM5500 | 0 | 0 | 0 | 0 | 0 | 0 |
| (25) Hydrochloric acid | 0 | 0 | 0 | 0 | 0 | 0 |
| (26) Preservative | 0.033 | 0.033 | 0.033 | 0.033 | 0.033 | 0.033 |
| (27) Sodium Xylene Sulfonate QS to viscosity target | QS | QS | QS | QS | QS | QS |
| (28) Citric Acid | 0.6 | 0.6 | 0.6 | 0.6 | 0.6 | 0.6 |
| (29) Sodium Benzoate | 0.15 | 0.15 | 0.15 | 0.15 | 0.15 | 0.15 |
| (30) Dimethicone DC330M | 0 | 0 | 0 | 0 | 0 | 0 |
| (31) Tetrasodium EDTA Tetrahydrate | 0.15 | 0.15 | 0.15 | 0.15 | 0.15 | 0.15 |
| (32) Water and Minors (QS to 100%) | QS | QS | QS | QS | QS | QS |
| (33) Blowing Agent A46 (Isobutane and Propane) | 5 | 5 | 5 | 5 | 5 | 5 |
| (34) Blowing Agent HF0 (Trans-1,3,3,3-tetrafluroprop-1-ene) | 0 | 0 | 0 | 0 | 0 | 0 |
| Total surfactant (active) | 9 | 13 | 13 | 12 | 13 | 13 |

| Ingredients | Ex. 26 | Ex. 27 | Ex. 28 | Ex. 29 | Ex. 30 | Ex. 31 |
|---|---|---|---|---|---|---|
| Form | Foam | Foam | Foam | Foam | Foam | Foam |
| (1) Sodium Deceyl Sulfate | 0 | 0 | 9 | 0 | 13 | 0 |
| (2) Sodium Deceth sulfate | 6 | 13 | 0 | 9 | 0 | 13 |
| (3) Sodium Laureth Sulfate (SLE1S) | 0 | 0 | 0 | 0 | 0 | 0 |
| (4) Sodium Laureth Sulfate (SLE3S) | 7 | 0 | 0 | 0 | 0 | 0 |
| (5) Sodium Lauryl sulfate | 0 | 0 | 0 | 0 | 0 | 0 |
| (6) Sodium Trideceth 2 sulfate | 0 | 0 | 4 | 4 | 0 | 0 |
| (7) Cocamidopropyl Betaine | 0 | 0 | 0 | 0 | 0 | 0 |
| (8) Cocamide MEA | 0 | 0 | 0 | 0 | 0 | 0 |
| (9) Sodium Laureth Sulfosuccinate | 0 | 0 | 0 | 0 | 0 | 0 |
| (10) Sodium Cocoyl Alaninate | 0 | 0 | 0 | 0 | 0 | 0 |
| (11) Sodium Lauroyl Sarcosinate | 0 | 0 | 0 | 0 | 0 | 0 |
| (12) Dehyrdroxyxanthan gum | 0.25 | 0.25 | 0 | 0 | 0.25 | 0 |
| (13) Glycol Distearate | 0 | 1.5 | 0 | 0 | 0 | 0 |
| (14) Glycerin | 0 | 0 | 0 | 0 | 0 | 0 |
| (15) Piroctone Olamine | 1 | 0.8 | 0.8 | 0.8 | 0.8 | 0.8 |

TABLE 2-continued

| Ingredient | | | | | | |
|---|---|---|---|---|---|---|
| (16) Zinc Pyrithione | 0 | 0 | 0 | 0 | 0 | 0 |
| (17) Zinc Carbonate | 0 | 0 | 0 | 0 | 0 | 0 |
| (18) Fragrance | 1.5 | 1.5 | 2 | 2 | 2 | 2 |
| (19) BF 17 HMW Guar | 0 | 0 | 0.5 | 0.5 | 0 | 0 |
| (20) Guar Hydroxypropyltrimonium Chloride (N-Hance 3196) | 0 | 0 | 0 | 0 | 0 | 0.4 |
| (21) Guar Hyrdroxypropyltrimonium Chloride (LMW) | 0 | 0 | 0 | 0 | 0.4 | 0 |
| (22) Polyquaternium 10 | 0 | 0 | 0 | 0 | 0.2 | 0.1 |
| (23) PEG23M | 0 | 0 | 0 | 0 | 0 | 0 |
| (24) Dimethicone DM5500 | 0 | 0 | 0 | 0 | 0 | 0 |
| (25) Hydrochloric acid | 0 | 0 | 0 | 0 | 0 | 0 |
| (26) Preservative | 0.033 | 0.033 | 0.033 | 0.033 | 0.033 | 0.033 |
| (27) Sodium Xylene Sulfonate QS to viscosity target | QS | QS | QS | QS | QS | QS |
| (28) Citric Acid | 0.6 | 0.6 | 0.6 | 0.6 | 0.6 | 0.6 |
| (29) Sodium Benzoate | 0.15 | 0.15 | 0.15 | 0.15 | 0.15 | 0.15 |
| (30) Dimethicone DC330M | 0 | 0 | 0 | 0 | 0 | 0 |
| (31) Tetrasodium EDTA Tetrahydrate | 0.15 | 0.15 | 0.15 | 0.15 | 0.15 | 0.15 |
| (32) Water and Minors (QS to 100%) | QS | QS | QS | QS | QS | QS |
| (33) Blowing Agent A46 (Isobutane and Propane) | 5 | 5 | 5 | 5 | 5 | 5 |
| (34) Blowing Agent HF0 (Trans-1,3,3,3-tetrafluroprop-1-ene) | 0 | 0 | 0 | 0 | 0 | 0 |
| Total surfactant (active) | 13 | 13 | 13 | 13 | 13 | 13 |
| pH | 5.5 | 5.5 | 5.5 | 5.5 | 5.5 | 5.5 |

| Ingredients | Ex. 32 | Ex. 33 | Ex. 34 | Ex. 35 | Ex. 36 | Ex. 37 |
|---|---|---|---|---|---|---|
| Form | Foam | Foam | Foam | Foam | Foam | Foam |
| (1) Sodium Deceyl Sulfate | 0 | 0 | 0 | 0 | 0 | 0 |
| (2) Sodium Deceth sulfate | 0 | 0 | 0 | 0 | 0 | 0 |
| (3) Sodium Laureth Sulfate (SLE1S) | 0 | 0 | 0 | 0 | 0 | 0 |
| (4) Sodium Laureth Sulfate (SLE3S) | 0 | 0 | 0 | 0 | 0 | 0 |
| (5) Sodium Lauryl sulfate | 0 | 0 | 0 | 0 | 0 | 0 |
| (6) Sodium Trideceth 2 sulfate | 0 | 0 | 0 | 0 | 0 | 0 |
| (7) Cocamidopropyl Betaine | 0 | 0 | 0 | 0 | 0 | 0 |
| (8) Cocamide MEA | 0 | 0 | 0 | 0 | 0 | 0 |
| (9) Sodium Laureth Sulfosuccinate | 0 | 0 | 13 | 0 | 0 | 9 |
| (10) Sodium Cocoyl Alaninate | 0 | 13 | 0 | 0 | 9 | 0 |
| (11) Sodium Lauroyl Sarcosinate | 13 | 0 | 0 | 9 | 0 | 0 |
| (12) Dehyrdroxyxanthan gum | 0.25 | 0.25 | 0.25 | 0.25 | 0.25 | 0.25 |
| (13) Glycol Distearate | 0 | 0 | 0 | 0 | 0 | 0 |
| (14) Glycerin | 0 | 0 | 0 | 2 | 2 | 2 |
| (15) Piroctone Olamine | 0.8 | 0.8 | 0.8 | 0.8 | 0.8 | 0.8 |
| (16) Zinc Pyrithione | 0 | 0 | 0 | 0 | 0 | 0 |
| (17) Zinc Carbonate | 0 | 0 | 0 | 0 | 0 | 0 |
| (18) Fragrance | 2 | 2 | 2 | 1.5 | 1.5 | 1.5 |
| (19) BF 17 HMW Guar | 0.4 | 0.4 | 0.4 | 0 | 0 | 0 |
| (20) Guar Hydroxypropyltrimonium Chloride (N-Hance 3196) | 0 | 0 | 0 | 0.4 | 0.4 | 0.4 |
| (21) Guar Hyrdroxypropyltrimonium Chloride (LMW) | 0 | 0 | 0 | 0.2 | 0.2 | 0.2 |
| (22) Polyquaternium 10 | 0 | 0 | 0 | 0 | 0 | 0 |
| (23) PEG23M | 0 | 0 | 0 | 0 | 0 | 0 |
| (24) Dimethicone DM5500 | 0 | 0 | 0 | 0 | 0 | 0 |
| (25) Hydrochloric acid | 0 | 0 | 0 | 0 | 0 | 0 |
| (26) Preservative | 0.033 | 0.033 | 0.033 | 0.033 | 0.033 | 0.033 |
| (27) Sodium Xylene Sulfonate QS to viscosity target | QS | QS | QS | QS | QS | QS |
| (28) Citric Acid | 0.6 | 0.6 | 0.6 | 0.6 | 0.6 | 0.6 |
| (29) Sodium Benzoate | 0.15 | 0.15 | 0.15 | 0.15 | 0.15 | 0.15 |
| (30) Dimethicone DC330M | 0 | 0 | 0 | 0 | 0 | 0 |
| (31) Tetrasodium EDTA Tetrahydrate | 0.15 | 0.15 | 0.15 | 0.15 | 0.15 | 0.15 |
| (32) Water and Minors (QS to 100%) | QS | QS | QS | QS | QS | QS |
| (33) Blowing Agent A46 (Isobutane and Propane) | 5 | 5 | 5 | 5 | 5 | 5 |
| (34) Blowing Agent HF0 (Trans-1,3,3,3-tetrafluroprop-1-ene) | 0 | 0 | 0 | 0 | 0 | 0 |

TABLE 2-continued

| | | | | | | |
|---|---|---|---|---|---|---|
| Total surfactant (active) | 13 | 13 | 13 | 13 | 13 | 13 |
| pH | 5.5 | 5.5 | 5.5 | 5.5 | 5.5 | 5.5 |

(1). Sodium Deceyl Sulfate from P&G Chemical
(2). Sodium Deceth sulfate from P&G Chemical
(3). Sodium Laureth-1 Sulfate from the Stepan Company
(4). Sodium Laureth-3 Sulfate from the Stepan Company
(5). Sodium Lauryl Sulfate from the Stepan Company
(6). Sodium Tridecyl Ether Sulfate - 2 mol from Solvay (Blue Island US)
(7). Cocamidopropyl betaine High pH from Stepan Co Millsdale (Elwood US)
(8). Cocamide monoethanolamine, CMEA from Stepan Company
(9). Sodium Laureth Sulfosuccinate from Stepan Company
(10). Sodium Cocoyl Alaninate from Sino Lion
(11). Sodium Lauroyl Sarcosinate from Stepan Company
(12). Dehyrdorxyxanthan gum Amaze XT (Akzo Nobel)
(13). Glycol Distearate from Golschmidt Chemical Company
(14). Glycerin from P&G Chemicals
(15). Piroctone Olamine (Octopirox from Clariant)
(16). Zinc Pyrithione, U2 ZPT from Lonza
(17). Zinc Carbonate from Bruggeman Group
(18). Fragrance from P&G Chemical
(19). Guar Hydroxypropyltrimonium Chloride, BF 17 HMW Guar from Ashland
(20). Guar Hydroxypropyltrimonium Chloride, NHance ™ 3196 from Ashland with a MW of 1,700,000 g/mol and charge density of 0.7 meq/g
(21). Guar Hydroxypropyltrimonium Chloride, Jaguar C500 from Solvay with a M. Wt of 500,000 g/mol and charge density of 0.8 meq/g
(22). Polyquaternium 10 from Dow Chemical
(23). Polyethylene Glycol, PEG 23M Polyox WSR N-1 2K from Amerchol Corp., Piscataway, NJ
(24). Dimethicone DM5500, Wacker Silicone
(25). Hydrochloric acid from Mallinckrodt Baker Inc.
(26). Preservative Kathon CG from Akzo Nobel
(27). Sodium Xylene Sulfonate from Stepan Company
(28). Citric Acid from Cargill Inc.
(29). Sodium Benzoate from Kalama Chemical
(30). Dimethicone, DC330M Momentive
(31). Tetrasodium EDTA Tetrahydrate
(32). Water from Misty Mountain Spring Water
(33). Blowing Agent A46 (Isobutane and Propane) Diversified Cpc International (Channahon US)
(34). Blowing Agent HF0 (Trans 1,3,3,3 Tetrafluroprop-1-ene) from Honey Well
35.

Methodology

A Single Product Context Aided Blind Test is placed to test low-surfactant foam anti-dandruff shampoo. The control for this test is a high surfactant foam shampoo formula containing 24% total surfactant. This summary contains panelist data from a post-use questionnaire. Panelist are asked to grade performance on a 5 point scale from 100 to 0. Data is reported as average ratings or % (Capital Letters indicate significantly better than the referenced examples: gray shaded=significantly worse vs control). FIG. 1 contains the formula details per leg. All tables are at 90% confidence.

These data show that for key attributes of the low surfactant foam shampoos examples 9, and 19 show parity "overall clean" response vs. high surfactant foam shampoo Example 3. Example 18 which contains PEG23M and low surfactant shows that it is directionally higher than all foams and significantly higher than the Example 19 which contains silicone which could make the consumers scalp/hair feel oily greasy. Parity to the high surfactant foam is also observed for the "overall hair and scalp feeling clean for a long time" and "overall mildness on hair and scalp." The consumer responses help to support that low surfactant foams example 9, 18, and 19 (12.5%) can clean just as well as high surfactant example 3 (24%) foam while delivering a mild cleaning experience. During the application lathering and rinsing step, consumers have identified the low surfactant foams to be just as easy to spread and rinse from the hair as the high surfactant foams. After rinsing example 9, and 18, consumers felt that their scalp are just as clean as high surfactant foam. Only example 19 which contains a, high concentration of silicone, results in a significantly lower score indicating less clean scalp. It has been observed that low surfactant formula 18 is parity to high surfactant example 3 for leaving roots feeling clean. Again, it may be hypothesized that PEG23M helps to deliver more clean feeling. For "scalp and hair feeling without unwanted residue after rinsing shampoo" it can be sees that all formulations are significantly better than the low surfactant example 19 contain high silicone concentration. All formulations show parity to high surfactant control for "easy to run fingers/combs though hair after rinsing shampoo." These formulation responses indicate good combability and thorough cleaning. After showering and washing panelist rate low surfactant PEG 23M containing example 18 parity to high surfactant example 3. for leaving scalp and roots feeling clean when damp after showering. Example 9 without PEG23M and Example 19 with PEG23M and silicone are significantly down for these questions. Finally, all formulations show parity to being easy to run fingers/comb though damp hair after showing again indicating clean, conditioned, and comb-able hair.

Examples/Combinations

A. A foaming composition comprising:
   a. from about 5% to about 13% total surfactant of one or more anionic surfactants;
   b. from 0.1% to about 2% of a surfactant soluble antidandruff active;
   c. from about 3% to about 15% of a blowing agent, wherein the foaming composition is at a pH of about 3.5 to 6.5.
B. A foaming composition according to Paragraph A, wherein the total surfactant of one or more anionic surfactants is from about 9% to about 13%.

C. A foaming composition according to Paragraph A-B, wherein the total surfactant of one or more anionic surfactants is from about 10% to about 13%.

D. A foaming composition according to Paragraph A-C, wherein the total surfactant of one or more anionic surfactants is from about 11% to about 13%.

E. A foaming composition according to Paragraph A-D, wherein the total surfactant of one or more anionic surfactants is from about 12% to about 13%.

F. A foaming composition according to Paragraph A-E, wherein the pH is from about 4 to about 6.

G. A foaming composition according to Paragraph A-F, wherein the pH is from about 5 to about 6.

H. A foaming composition according to Paragraph A-G, wherein the surfactant soluble antidandruff active is from about 0.6% to about 1%.

I. A foaming composition according to Paragraph A-H, wherein the surfactant soluble antidandruff active is from about 0.5% to about 0.8%.

J. A foaming composition according to Paragraph A-I, wherein the anti-dandruff deposition is equal to or greater than 0.8 microgram per $cm^2$.

K. A foaming composition according to Paragraph A-G, the foam density is 0.01 $g/cm^3$ to about 0.2 $g/cm^3$.

L. A foaming composition according to Paragraph A-G, wherein the foam density is 0.05 $g/cm^3$ to about 0.1 $g/cm^3$.

M. A foaming composition according to Paragraph A-L, wherein the foam comprises a bubble size distribution comprising an $R_{32}$ of from about 5 μm to about 90 μm.

N. A foaming composition according to Paragraph A-M, wherein the foam comprises a yield point of from about 10 Pa to about 50 Pa.

O. A foaming composition according to Paragraph A-N, wherein the viscosity (measured at 25 C) is less than 3,000 cps.

P. A foaming composition according to Paragraph A-O, wherein the composition further comprises from about 1% to about 5% of one or more amphoteric/zwitterionic or nonionic co-surfactants, and mixtures thereof.

Q. A foaming composition according to Paragraph A-P, wherein the viscosity modifiers with a molecular weight of from about 75 g/mol to about 350 g/mol.

R. A foaming composition according to Paragraph A-Q, wherein the blowing agent is from about 1% to about 15%.

S. A foaming composition according to Paragraph A-R, wherein the composition further comprises from 0.1% to 5% of a stabilizing agent.

T. A foaming composition according to Paragraph A-S, wherein the stabilizing agent is selected from the group consisting of trihydroxystearin, ethylene glycol distearate polymers, and mixtures thereof.

U. A foaming composition according to Paragraph A-T, wherein the viscosity modifier is selected from the group consisting of ethanol, dipropylene glycol, sodium xylene sulfonate, sodium chloride, alkoxylated silicone/ethoxylated silicone/propoxylated silicone/polyoxyethylene silicone/polyoxypropylene silicone/polyethyleneglycol silicone/PEG-8 silicone/PEG-9 silicone/PEG-n silicone/silicone ether (n could be another integer), and mixtures thereof.

V. A foaming composition according to Paragraph A-U, further comprising an anti-dandruff particulate selected from the group consisting of pyridinethione salts, selenium sulfide, particulate sulfur, and mixtures thereof.

W. A foaming composition according to Paragraph A-V, wherein surfactant soluble agent is selected from the group consisting of an azole, piroctone olamine, N-Hydroxy-6-octyloxypyridine-2(1H)one, hexamidine diisethionate and mixtures thereof, X. A foaming composition according to Paragraph A-W, wherein the co-surfactant is selected from the group consisting of lauramidopropyl betaine, cocoamidopropyl betaine, lauryl hydroxysultaine, sodium lauroamphoacetate, coco monoethanolamide, and mixtures thereof.

Y. A foaming composition according to Paragraph A-X, wherein the blowing agent is selected from the group consisting of propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, CO2, and mixtures thereof.

Z. A foaming composition according to Paragraph A-Y, wherein the blowing agent is selected from the group consisting of propane and isobutene, trans-1,3,3,3-tetrafluoropropene, and mixtures thereof.

AA. A foaming composition according to Paragraph A-Z, wherein the composition further comprises a cationic polymer.

BB. A foaming composition according to Paragraph A-AA, wherein the composition further comprises a conditioning agent.

CC. A foaming composition according to Paragraph A-BB, wherein the conditioning agent is a silicone.

DD. A foaming composition according to Paragraph A-CC wherein the foaming composition has a deposition efficiency of >1.7× that of a control composition that deposits about 1% of a mass of surfactant soluble antidandruff active dosed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A foaming composition comprising:
   a. from about 5% to about 13% total surfactant of one or more anionic surfactants;
   b. from 0.1% to about 2% of a surfactant soluble anti-dandruff active;
   c. from about 3% to about 15% of a blowing agent, wherein the foaming composition is at a pH of about 3.5 to 6.5 and wherein the foaming composition has a deposition efficiency of >1.7× that of a liquid control composition comprising a total surfactant (active) of about 17% that deposits about 1% of a mass of surfactant soluble antidandruff active dosed.

2. A foaming composition according to claim 1 wherein the total surfactant of one or more anionic surfactants is from about 9% to about 13%.

3. A foaming composition according to claim 1 wherein the total surfactant of one or more anionic surfactants is from about 10% to about 13%.

4. A foaming composition according to claim 1 wherein the total surfactant of one or more anionic surfactants is from about 11% to about 13%.

5. A foaming composition according to claim 1 wherein the total surfactant of one or more anionic surfactants is from about 12% to about 13%.

6. A foaming composition according to claim 1 wherein the pH is from about 4 to about 6.

7. A foaming composition according to claim 1 wherein the pH is from about 5 to about 6.

8. A foaming composition according to claim 1 wherein the surfactant soluble antidandruff active is from about 0.6% to about 1%.

9. A foaming composition according to claim 1 wherein the surfactant soluble antidandruff active is from about 0.5% to about 0.8%.

10. A foaming composition according to claim 1 wherein the foaming composition has an-anti-dandruff deposition is equal to or greater than 0.8 microgram per $cm^2$.

11. A foaming composition according to claim 1 wherein the foaming composition has a foam density is 0.01 $g/cm^3$ to about 0.2 $g/cm^3$.

12. A foaming composition according to claim 1 wherein the foam density is 0.05 $g/cm^3$ to about 0.1 $g/cm^3$.

13. A foaming composition according to claim 1 wherein the foaming composition has a foam comprising a bubble size distribution comprising an $R_{32}$ of from about 15 μm to about 50 μm.

14. A foaming composition according to claim 1 wherein the foaming composition has a foam comprising a yield point of from about 10 Pa to about 50 Pa.

15. A foaming composition according to claim 1 wherein the foaming composition has a viscosity (measured at 25 C) less than 3,000 cps.

16. A foaming composition according to claim 1 wherein the composition further comprises from about 1% to about 5% of one or more amphoteric/zwitterionic or nonionic co-surfactants, and mixtures thereof.

17. A foaming composition according to claim 1 wherein the foaming composition comprises viscosity modifiers with a molecular weight of from about 75 g/mol to about 350 g/mol.

18. A foaming composition according to claim 1 wherein the blowing agent is from about 4% to about 7%.

19. A foaming composition according to claim 1 wherein the composition further comprises from 0.1% to 5% of a stabilizing agent.

20. A foaming composition according to claim 19 wherein the stabilizing agent is selected from the group consisting of trihydroxystearin, ethylene glycol distearate polymers, and mixtures thereof.

21. A foaming composition according to claim 17 wherein the viscosity modifier is selected from the group consisting of ethanol, dipropylene glycol, sodium xylene sulfonate, sodium chloride, alkoxylated silicone/ethoxylated silicone/propoxylated silicone/polyoxyethylene silicone/polyoxypropylene silicone/polyethyleneglycol silicone/PEG-8 silicone/PEG-9 silicone/PEG-n silicone/silicone ether (n could be another integer), and mixtures thereof.

22. A foaming composition according to claim 1 further comprising an anti-dandruff particulate selected from the group consisting of pyridinethione salts, selenium sulfide, particulate sulfur, and mixtures thereof.

23. A foaming composition according to claim 1 wherein surfactant soluble agent is selected from the group consisting of an azole, piroctone olamine, N-Hydroxy-6-octyloxy-pyridine-2(1H)one, hexamidine diisethionate and mixtures thereof.

24. A foaming composition according to claim 1 wherein the foaming composition comprises a co-surfactant selected from the group consisting of lauramidopropyl betaine, cocoamidopropyl betaine, lauryl hydroxysultaine, sodium lauroamphoacetate, coco monoethanolamide, and mixtures thereof.

25. A foaming composition according to claim 1 wherein the blowing agent is selected from the group consisting of propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, CO2, and mixtures thereof.

26. A foaming composition according to claim 25 wherein the blowing agent is selected from the group consisting of propane and isobutene, trans-1,3,3,3-tetrafluoropropene, and mixtures thereof.

27. A foaming composition according to claim 1 wherein the foaming composition further comprises a cationic polymer.

28. A foaming composition according to claim 1 wherein the foaming composition further comprises a conditioning agent.

29. A foaming composition according to claim 28 wherein the conditioning agent is a silicone.

* * * * *